United States Patent
Germond et al.

(10) Patent No.: US 6,929,931 B1
(45) Date of Patent: Aug. 16, 2005

(54) **EXPRESSION CONTRUCTS USING *LACTOBACILLUS DELBRUECKII* SUBSP. LACTIS LAC REPRESSOR PROTEIN AND ITS LAC REPRESSOR BINDING SITE, MICROORGANISMS AND METHODS THEREOF**

(75) Inventors: Jacques Edouard Germond, Crissier (CH); Luciane LaPierre, Attalens (CH); Beat Mollet, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 10/019,817
(22) PCT Filed: Jun. 23, 2000
(86) PCT No.: PCT/EP00/05834
§ 371 (c)(1),
(2), (4) Date: May 13, 2000
(87) PCT Pub. No.: WO01/02576
PCT Pub. Date: Jan. 11, 2001

(30) Foreign Application Priority Data
Jun. 30, 1999 (EP) .............................................. 99112471

(51) Int. Cl.$^7$ ............................................... C12P 21/06
(52) U.S. Cl. ................ 435/69.1; 435/320.1; 435/252.3; 435/254.1; 435/183
(58) Field of Search ........................... 435/320.1, 252.3, 435/254.1, 69.1, 183, 252.1, 252.9; 536/23.1, 23.7; 426/7

(56) References Cited

U.S. PATENT DOCUMENTS 5,676,985 A   10/1997  Fletcher et al.

FOREIGN PATENT DOCUMENTS

EP     0 643 137 A1    3/1995
WO     WO 93/17117     9/1993

OTHER PUBLICATIONS

Germond et al. Evolution of the Bacterial species *Lactobacillus delbrueckii*: A partial Genomic Study with Reflections on Prokaryotic Species Concept. Mol. Biol. Evol. (2003) 20(1):93–104.*

Lapierre et al. Regulation and Adaptive Evolution of Lactose Operon Expression in *Lactobacillus delbrueckii*. J. Bacteriol. (2002) 184(4):928–935.*

Laemmli, U. K., *Cleavage of Structural Proteins during the Assembly of the Head of Bacteriophage T4*, Nature, vol. 227, Aug. 15, 1970, pp. 680–685.

Bergmeyer, *Methods of Enzymatic Analysis*, vol. 2, 1983, pp. 206–209.

Chassy et al., *Molecular characterization of the plasmid–encoded lactose–PTS of Lactobacillus casei*, FEMS Microbiology Reviews, vol. 63 (1989) pp. 157–166.

Robert M. Horton, *PCR–Mediated Recombination and Mutagenesis*, Molecular Biotechnology, vol. 3 (1995) pp. 93–95.

Germond et al., *A new genetic element in Lactobacillus delbrueckii subsp. bulgaricus*, Mol. Gen. Genet., vol. 248 (1995) pp. 407–416.

Gasson et al., *Plasmid Complements of Streptococcus lactis NCDO 712 and Other Lactic Streptococci After Protoplast–Induced Curing*, Journal of Bacteriology, vol. 154, No. 1, Apr. 1983, pp. 1–9.

Sanger et al., *DNA sequencing with chain–terminating inhibitors*, Proc. Natl. Acad. Sci. USA, vol. 74, No. 12, Dec. 1977, pp. 5463–5467.

Platteeuw et al., *Use of the Escherichia coli β–Glucuronidase (gusA) Genes as a Reporter Gene for Analyzing Promoters in Lactic Acid Bacteria*, Applied and Environmental Microbiology, vol. 60, No. 2, Feb. 1994, pp. 587–593.

Holo et al., *High–Frequency Transformation, by Electroporation, of Lactococcus lactis subsp. cremoris Grown with Clycine in Osmotically Stabilized Media*, Applied and Environmental Microbiology, vol. 55, No. 12, Dec. 1989, pp. 3119–3123.

Delley et al., *DNA Probe for Lactobacillus delbrueckii*, Applied and Environmental Microbiology, vol. 56, No. 6, Jun. 1990, pp. 1967–1970.

Weickert et al., *Site–directed mutagenesis of a catabolite repression operator sequence in Bacillus subtilis*, Proc. Natl. Acad. Sci. USA, vol. 87, Aug. 1990, pp. 6238–6242.

Schmidt et al., *Expression and Nucleotide Sequence of the Lactobacillus bulgaricus β–Galactosidase Gene Cloned in Escherichia coli*, Journal of Bacteriology, Feb. 1989, pp. 625–635.

Leong–Morgenthaler et al., *Lactose Metabolism in Lactobacillus bulgaricus: Analysis of the Primary Structure and Expression of the Genes Involved*, Journal of Bacteriology, vol. 173, No. 6, Mar. 1991, pp. 1951–1957.

Poolman et al., *Lactose Transport System of Streptococcus thermophilus: a Hybrid Protein with Homology to the Melibiose Carrier and Enzyme III of Phosphoenolpyruvate–Dependent Phosphotransferase Systems*, Journal of Bacteriology, vol. 171, No. 1, Jan. 1989, pp. 244–253.

Oskouian et al., *Cloning and Characterization of the Repressor Gene of the Staphylococcus aureus Lactose Operon*, Journal of Bacteriology, vol. 169, No. 12, Dec. 1987, pp. 5459–5465.

(Continued)

Primary Examiner—Kathleen Kerr
(74) Attorney, Agent, or Firm—Bell, Boyd & Lloyd LLC

(57) ABSTRACT

A DNA sequence suitable for the controlled transcription and/or expression of a variety of different genes in bacteria, preferably gram positive bacteria is provided. In particular, the DNA sequence includes the promoter and the gene coding for the lac repressor of the lac operon of *Lactobacillus delbrueckii* with a DNA sequence coding for a gene product of interest being arranged inbetween.

17 Claims, 9 Drawing Sheets

OTHER PUBLICATIONS

Figure 5:
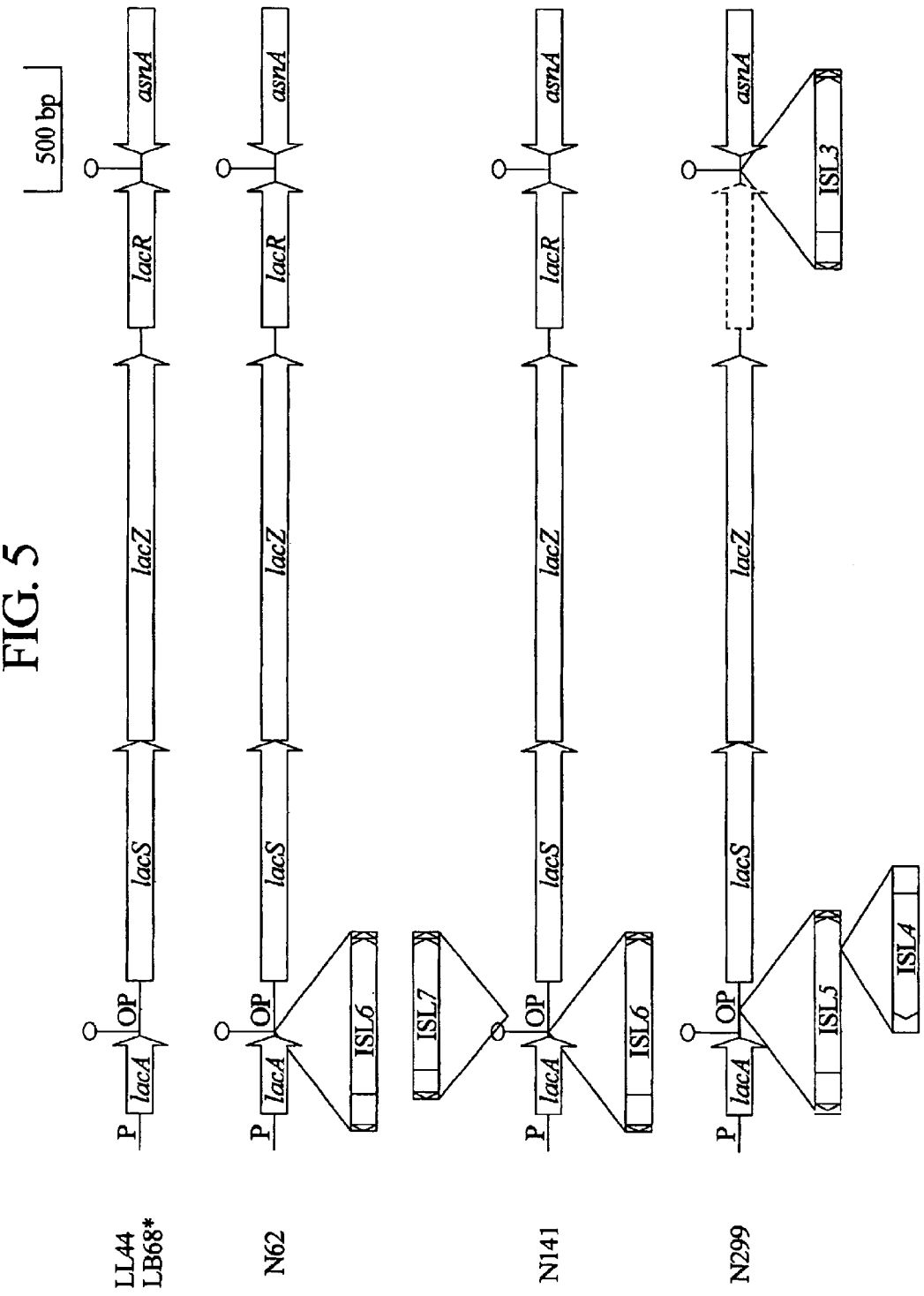

Van Rooijen et al., *Molecular Cloning, Transcriptional Analysis, and Nucleotide Sequence of lacR, a Gene Encoding the Repressor of the Lactose Phosphotransferase System of Lactococcus lactis*, The Journal of Biological Chemistry, vol. 265, No. 30, Oct. 1990, pp. 18499–18503.

Schroeder et al., *Analysis of the lacZ sequences from two Streptococcus thermophilus strains: comparison with the Escherichia coli and Lactobacillus bulgaricus β–galactosidase sequences*, Journal of General Microbiology, vol. 137 (1991) pp. 369–380.

Terzaghi et al., *Improved Medium for Lactic Streptococci and Their Bacteriophages*, Applied Microbiology, Jun. 1975, vol. 29, No. 6, pp. 807–813.

Devereux et al., *A comprehensive set of seqence analysis programs for the VAX*, Nucleic Acids Research, (1984) vol. 12, No. 1, pp. 387–395.

W. V. Shaw, *Chloramphenicol Acetytransferase assay*, Methods Enzymol. vol. 43 (1975) pp. 737–755.

Marion M. Bradford, *A Rapid and Sensitive Method for the Qauntitation of Microgram Quantities of Protein utilizing the Principle of Protein–Dye Binding*, Anal. Biochem., vol. 12 (1976) pp. 248–254.

DeMan et al., *A medium for the cultivation of lactobacilli*, J. Appl. Bacteriol., vol. 23 (1960) pp. 130–135.

Leong–Morgenthaler et al., "Lactose Metabolism in *Lactobacillus bulgaricus*: Analysis of the Primary Structure and Expression of the Genes Involved"—*Journal of Bacteriology*, Mar. 1991, p. 1951–1957.

Dubendorff et al., "Controlling Basal Expression in an Inducible T7 Expression System by Blocking the Target T7 Promoter with lac Repressor"—*J. Mol. Biol.*, (1991) 219, 45–59.

Adjic et al., "Organization and Nucleotide Sequence of the Streptococcus mutans galactose operon"—*Gene*, 180 (1996) 137–144.

* cited by examiner

FIG. 1

O1

```
                   853           860              870           880
LL44, LB68  ..T G T T T A C T A A A A A T A T T T T G G T A A A G C A
               ←―――――――――→  ←―――――→     ――――――→ ―――――→ →

N62, LB10   ..T G T T T A C T A A A A G T A T T T T G G T A A A A C A
               ←―――――――――→  ←―――――→     ――――――→ ―――――→ →

N141        ..T G G C G A C T A A A A G T A T T T T G G T A A A A C A
               ISL7       ← ←―――――→     ――――――→ ――→ →

N299        ..A A A T T A C T A A A A A T A T T T T A G T A A A A C A
               ISL5         ←―――――――→           ――――――――→
```

O2

```
                              890           900
LL44, LB68   T C T T G A T T T G T T T A G T A A A C G G G T C T A T A...
                    ←―――――  ←―――――――→  ――――――→ ―――――→

N62, LB10    T C T T G A T T T G T T T A G T A A A C A A G T C T A T A...
                    ←―――――  ←―――――――→  ――――――→ ―――――→

N141         T C T T G A T T T G T T T A G T A A A C A A G T C T A T A...
                    ←―――――  ←―――――――→  ――――――――――→ ――→ →

N299         T C T T G G T T T A T T T A G T A A A C A A G T C T A T A...
                    ←―――――  ←―――――――→  ――――――→
```

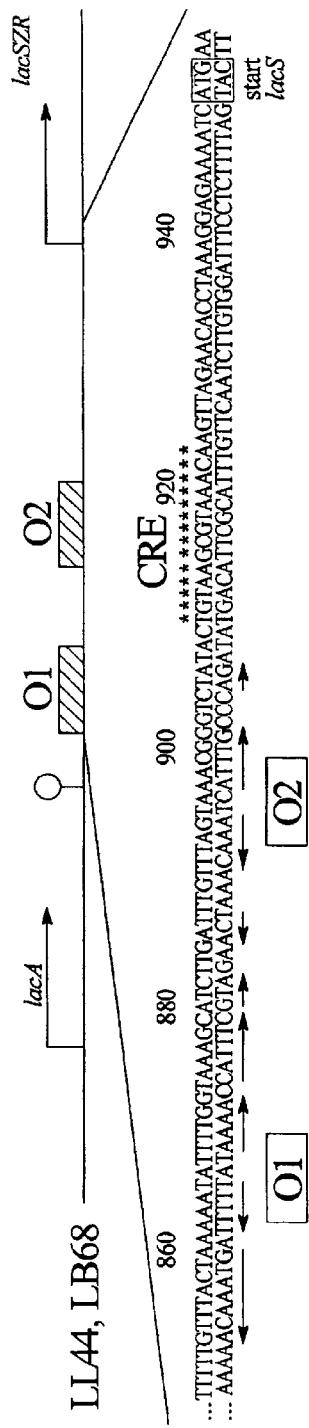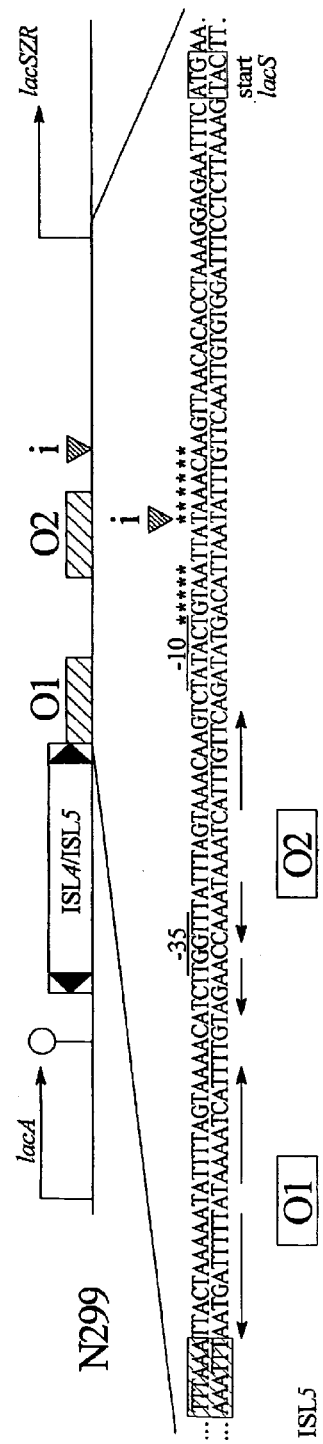

FIG. 4

```
   1 GAATTTTGTCTGGATGCTCAGGAAGCCCGCCAGCTCAAGCTGGTGATTCAGCCACTTTTT
            stop lacZ                                    RBS
  61 ACTGAA TAA TGCTACAATTGACTTAACAGCATAAAATTTTAGTAAAAGCGAGTGAAGAAG 121 ATG GCAACGATCAGAGAAGTGGCCAAGGCAGCCGGCGTGTCGCCAGCGACGGTTTCCCGG
   1  M   A  T  I  R  E  V  A  K  A  A  G  V  S  P  A  T  V  S  R
                helix                turn              helix 181 GTCTTGAACTATGACCAGACCCTGTCGGTCAATGAGGCAACGCGGCAGAAGATATTCAAA
  21  V  L  N  Y  D  Q  T  L  S  V  N  E  A  T  R  Q  K  I  F  K 241 ACTGCTGAAGCCATGCACTACCATAAGAGCCGGAAGACCAGAAAGAGCAAGCAAAAGCGC
  41  T  A  E  A  M  H  Y  H  K  S  R  K  T  R  K  S  K  Q  K  R 301 CTGGCGATCTGCCTGTGGTGTGACCAAGACCAGGAGATCAAGGACCTCTATTACTATTCA
  61  L  A  I  C  L  W  C  D  Q  D  Q  E  I  K  D  L  Y  Y  Y  S 361 ATCAGAACCAGCGCGCAAGCAGAGGCCAAGAAGCAGGGACTTGAAAGCCAGGTCATTTAT
  81  I  R  T  S  A  Q  A  E  A  K  K  Q  G  L  E  S  Q  V  I  Y 421 CCGGCTGATCCTTTGCCCGATCCAGCTGCTTTAAGCGGGATTATCATGATTGGCTACCAG
 101  P  A  D  P  L  P  D  P  A  A  L  S  G  I  I  M  I  G  Y  Q 481 CAGTATTCGCCAGACCGCTTGAATGAAGTCAAAAAGTCTGGCCTGCCCCTGGTCTTTGTC
 121  Q  Y  S  P  D  R  L  N  E  V  K  K  S  G  L  P  L  V  F  V 541 GATACTGACACCTTAAAATTGGGTTACTGCTCAGTTGTGGCTGACTTTGGCCAGGCCATG
 141  D  T  D  T  L  K  L  G  Y  C  S  V  V  A  D  F  G  Q  A  M 601 CAGGAGGCGCTAGAGGTCTTCTGGGGGCAGGGCAGGGAGCGGATCGCCCTTTTGGATGGT
 161  Q  E  A  L  E  V  F  W  G  Q  G  R  E  R  I  A  L  L  D  G 661 GATTTGGACAGTAATTTTGATAAAAACAACTTGGTCGACTTCCGCTTCCGCGATTATAAG
 181  D  L  D  S  N  F  D  K  N  N  L  V  D  F  R  F  R  D  Y  K
                                        ▼
 721 AAGAGCCTCGCGGCCCGCGGCCAGTACGACCCGGACTTAGTCTATGTTGGAAACTTCACT
 201  K  S  L  A  A  R  G  Q  Y  D  P  D  L  V  Y  V  G  N  F  T 781 CCGCAATCTGGCTATGAAGCCATTAAAGAAGCTCTTAAGTCCGGCTCCTTCCCGAAAGCC
 221  P  Q  S  G  Y  E  A  I  K  E  A  L  K  S  G  S  F  P  K  A 841 TTGATTGCGGCTAATGACGCCATGGCTATTGGAGCATTGAAGGCCTTTAAAGAAGCTGGA
 241  L  I  A  A  N  D  A  M  A  I  G  A  L  K  A  F  K  E  A  G 901 ATTAAAGTCCCAGAGGACGTCAGTCTGATTTCTTTTAATGACACAACGGCAGCAGAATTT
 261  I  K  V  P  E  D  V  S  L  I  S  F  N  D  T  T  A  A  E  F 961 GCCAACCCAGCCTTGACTAGCGTACATGTAGAGACC CAG CAGATGGGCCGAGCCAGCGTC
 281  A  N  P  A  L  T  S  V  H  V  E  T  Q  Q  M  G  R  A  S  V 1021 AAGGTCATGAAAGACCTGCTGGATGATGATGAAGCCGGCACTTACAAGGTCACTTTCCCA
 301  K  V  M  K  D  L  L  D  D  D  E  A  G  T  Y  K  V  T  F  P 1081 ACAAAACTCGTTTACCGGGAATCTTGCCCAAAAGCATAAGGGCATAGAGCATAATAACAG
 321  T  K  L  V  Y  R  E  S  C  P  K  A  *

1141 CAAAGAAATAGCTTGGAGATTGATTTTCTCCAAGCTATTTTTCGTATATA TTA TGGCTGC
                                                      stop asnA 1201 ATTCTGTTGATCATTCTTGGGAATGGGACAGCTTCACGAACGTGGTCCAGCTTGCAGATC
1261 CAGGCAATGACCCGTTCAAAG
```

FIG. 10
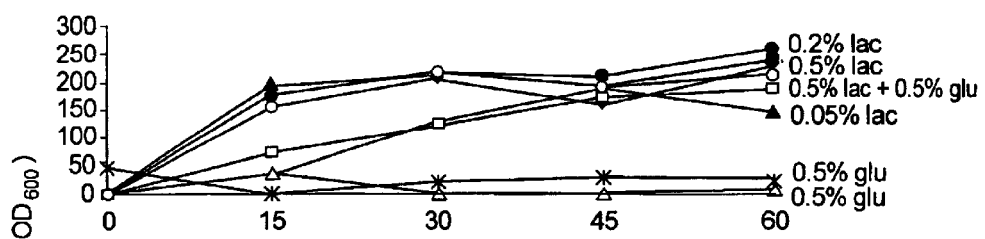
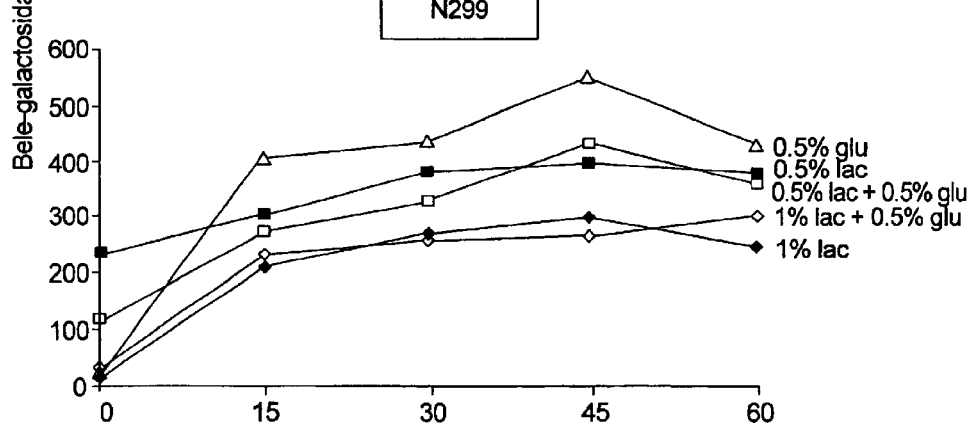

EXPRESSION CONTRUCTS USING *LACTOBACILLUS DELBRUECKII* SUBSP. LACTIS LAC REPRESSOR PROTEIN AND ITS LAC REPRESSOR BINDING SITE, MICROORGANISMS AND METHODS THEREOF

The present invention relates to a DNA sequence suitable for controlled transcription and/or expression of a variety of different genes in bacteria, preferably in gram positive bacteria. In particular, the present invention pertains to a DNA sequence comprising the promoter/operator region of the lac operon of *Lactobacillus delbrueckii* with a DNA sequence coding for a gene product of interest being arranged in functional relationship therewith.

In the food industry a variety of different lactic acid bacteria are used to prepare food products, such as cheese, buttermilk or yogurt, essentially relying on the fermentative activity of said bacteria. For this purpose bacteria of e.g. the genus *Streptococcus* or *Lactobacillus* are put to use, with their primary function being to convert sugar, such as lactose or glucose, to lactic acid and to produce a satisfying texture and aroma.

A problem of any such fermentation resides in that the end product of the metabolic process, lactic acid, is often produced abundantly rendering the dairy product acid to an extent not accepted by most of the consumers. Thus, the persons attending the production process must take care so as to control the progress of the manufacturing process in order to avoid any detrimental effects of an excessive fermentation to the food product.

Lactic acid bacteria have also been used as fermenting agents for the preservation of food taking benefit of a low pH and the action of fermentation products generated during the fermentation process to inhibit the growth of spoilage bacteria. Also in such cases it is up to the personal to control the biological activity of the microorganisms and to bring the production process at a desired stage to a stop.

Therefore, there is a need in the art to control the fermentative activity of microorganisms used for the production of food, thus being capable to provide a fermentation up to a desired stage of the production process of the food product without involving too much labor work from the side of the attending staff.

In the recent past producers have tried to add valuable properties to bacteria utilized in fermentative processes via recombinant technologies. To this end, a vector bearing a homologous or heterologous gene coding for a polypeptide of interest is brought into the bacterial cell to either remain extra-chromosomal or to be inserted in the bacteria's chromosome. Expression is then effected by means of a heterologous promoter linked to the respective gene, which may be controlled as desired.

Though a control of the expression of the heterologous gene may be achieved thereby, this procedure is disadvantageous in that the regulon used to control the expression of the desired gene is in most cases exogeneous to the bacteria. Yet, the use of foreign gene material in bacteria utilized for the preparation of food products is presently not accepted by the consumer.

An object of the present invention is to provide means for a controlled transcription/expression of genes in bacteria that do not exhibit the disadvantages of the prior art techniques.

The above object has been solved by providing a DNA sequence exhibiting the following general formula $$p/o\text{-}(A)_n\text{-}R_y, \text{ or}$$

$$p/o\text{-}R_y\text{-}(A)_n$$

wherein p/o denotes the DNA sequence identified under SEQ ID No. 9 or a functional variant thereof, which retains the capability to bind the lac repressor protein of *Lactobacillus delbrueckii*; A denotes a gene coding for a polypeptide of interest; n denotes an integer of $\geq 0$; R denotes the gene coding for the lacR repressor protein as identified under SEQ ID No. 2 or a functional variant thereof; and Y is 0 or 1.

Consequently, in case y=0 the gene coding for the lac repressor protein may be situated at any site of the bacteria's chromosome and may be subject to any suitable promoter region such that is e.g. expressed constitutively.

According to a preferred embodiment the DNA sequence is represented by the general formula $p/o\text{-}(A)_n\text{-}R$ or $p/o\text{-}R\text{-}(A)_n$, respectively, with p, A and R being as identified above. In this case, i.e. in the case of Y=1, the construct is composed of three components, the promoter/operator region, the gene coding for the polypeptide of interest and the gene coding for the lac repressor protein (lacR), with the genes coding for the respective polypeptides (A, lacR) being arranged in either order. The lacR gene is such subject to its own promoter/operator. In addition, the gene coding for the lacR protein may be arranged such that its transcriptional direction is opposite to that of the gene A coding for the polypeptide of interest.

According to another preferred embodiment the gene coding for a polypeptide of interest is selected from group consisting of genes encoding enzymes, cell surface proteins or functional peptides, such as e.g. dextransucrase, glycosyltransferase, phytase, transglutaminase, peptidase, phenylalanine ammonia lyase, protease, cell surface antigens, bacteriocins, hormones, insulin.

The promoter region may also lack any catabolite responsive elements, so that no repression in the presence of a particular carbon source may be effected.

According to another preferred embodiment the DNA sequence is used to transform a microorganism, which is preferably a gram positive bacterium or more preferably a microorganism selected from the group consisting of lactic acid bacteria, such as *Lactococcus, Lactobacillus, Streptococcus, Leuconostoc* etc.

The DNA sequence may be incorporated into the respective microorganism by means of an appropriate vector, such as a plasmid or a viral construct, and may remain in the microorganism extra-chromosomal. Yet, according to another preferred embodiment the construct may also be inserted into the bacteria's chromosome by means of conjugation followed by a crossing over between the plasmid and a homologous chromosomal sequence, or direct transformation and single or double cross over integration.

The DNA construct according to the present invention may therefore suitably be used for the transcription and/or expression of gene products, such as RNA or polypeptides.

In the figures,

FIG. 1 shows a comparison of *L. delbrueckii* operator sequences (O1 and O2) as represented by SEQ ID NOS: 22–27. Arrows are for inverted repeats. The LL44 sequence is numbered according to FIG. 1. Sequence of the second helix of lacR (repressor) is indicated.

FIG. 2 shows the organization of the promoter region of the *L. delbrueckii* LL44 and LB68 lac operon as represented by SEQ ID NOS: 30 and 31. Operators O1 and O2 are indicated by darkened boxes. The inverted repeats of the operators are represented by arrows. The sequence responsible for catabolite repression (CRE) is overdrawn by stars. The promoter sequence of LL44 is numbered according to FIG. 1.

FIG. 3 shows the organization of the promoter region of the *L. delbrueckii* N299 lac operon as represented by SEQ ID NOS: 32 and 33. Operators O1 and O2 are indicated by darkened boxes. The inverted repeats of the operators are represented by arrows. The sequence responsible for catabolite repression (CRE) is overdrawn by stars. The inverted repeat of ISL5 is boxed and shaded. The initiation of transcription is shown by an i (arrow head) (Leong-Morgenthaler et al. 1991).

FIG. 4 shows the nucleotide and amino acid sequence of the *L. delbrueckii* subsp. *lactis* LL44 lacR gene as represented by nucleotides 1–1281 of SEQ ID NO: 1 and SEQ ID NO: 2, respectively. Start (121) and stop (1119) codons are boxed. Putative lacR RBS is underlined. The putative rho-independent terminator is underlined by convergent arrows. Stop codons of the beta-galactosidase (lacZ) and Asn t-RNA synthetase (asnA) genes are boxed. Insertion sequence of ISL3 is represented by a large open arrow. Single base pair deletion (722) in the mutant LZL102 is shown by an arrow head, leading to a premature stop codon (758) underlined.

FIG. 5 shows a physical map of the lactose operon of different *L. delbrueckii* strains. Open arrows are for the lac operon genes, and dashed arrow is for inactivated lacR. Boxes are for the different IS-elements, where the arrows heads are for the inverted repeats. The * indicates that LB68 has the same sequence as LL44 except an insertion in the 5' and of the lacA gene.

Figure 6:
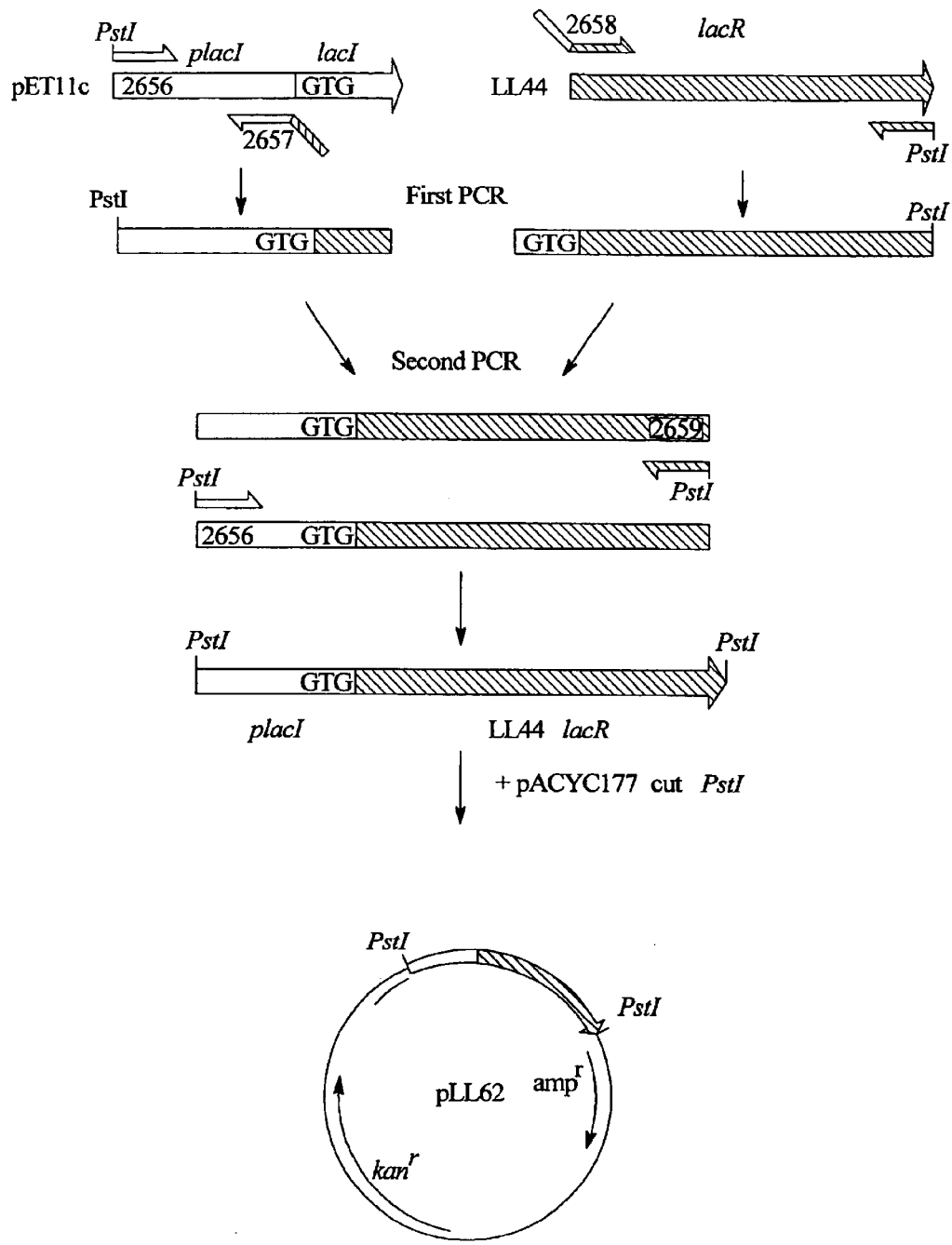

FIG. 6 shows a schematic representation of the construction of pLL62. The darkened box is for LL44 lacR gene, and the white box is for the promoter region of the lacI gene of pET11c. Both were linked by PCR amplification using the SOEing method.

Figure 7:
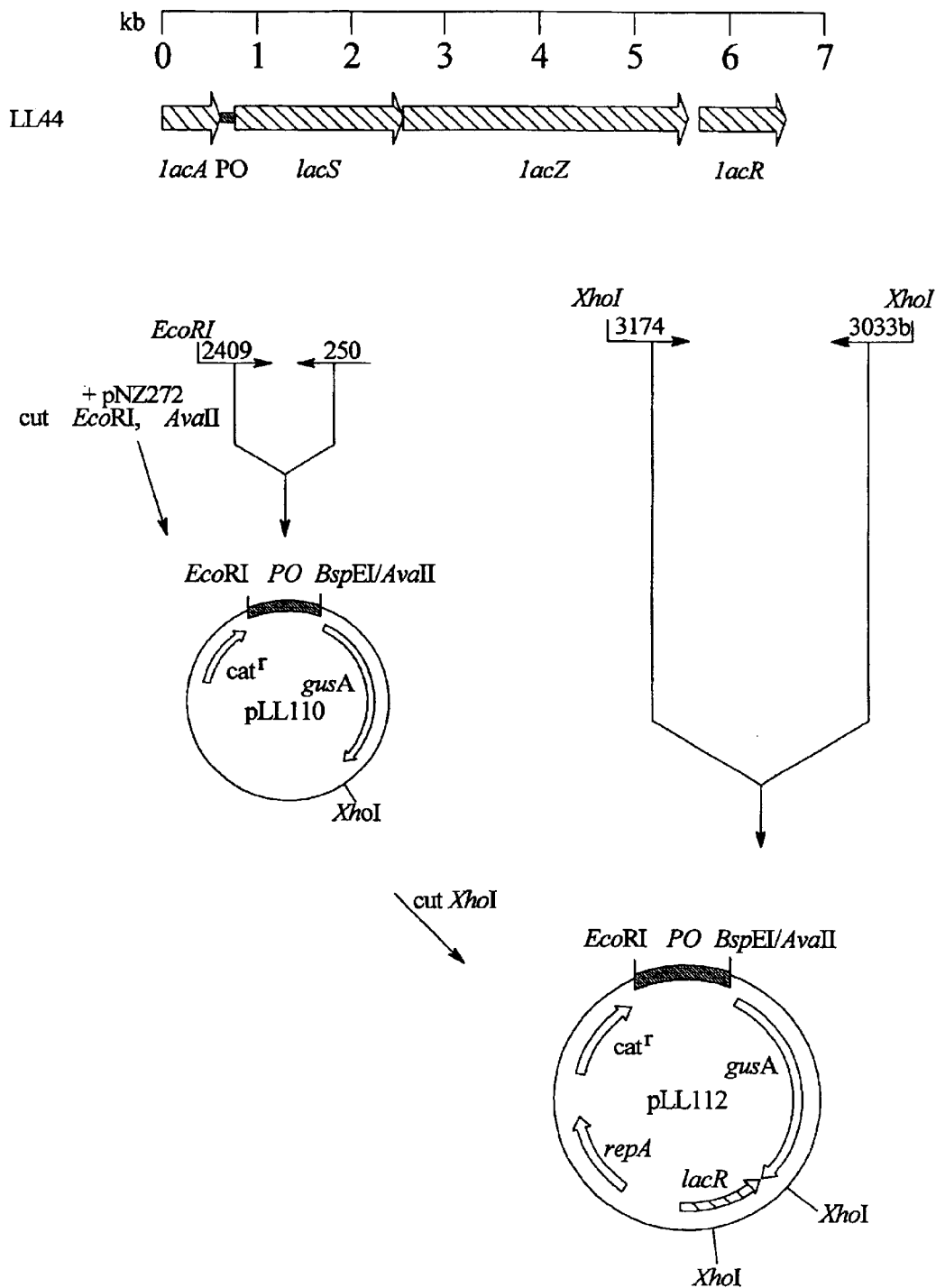

FIG. 7 shows a schematic representation of the construction of a pLL110 and pLL112 (CNCM I-2089). Dashed arrows are for the genes of the *L. delbrueckii* lac operon, and open arrows for plasmid genes. The darkened box is for the promoter region cloned in front of the gusA gene. Plasmids are not drawn to scale. The simple arrows represent the primers used to amplify the cloned regions.

Figure 8:
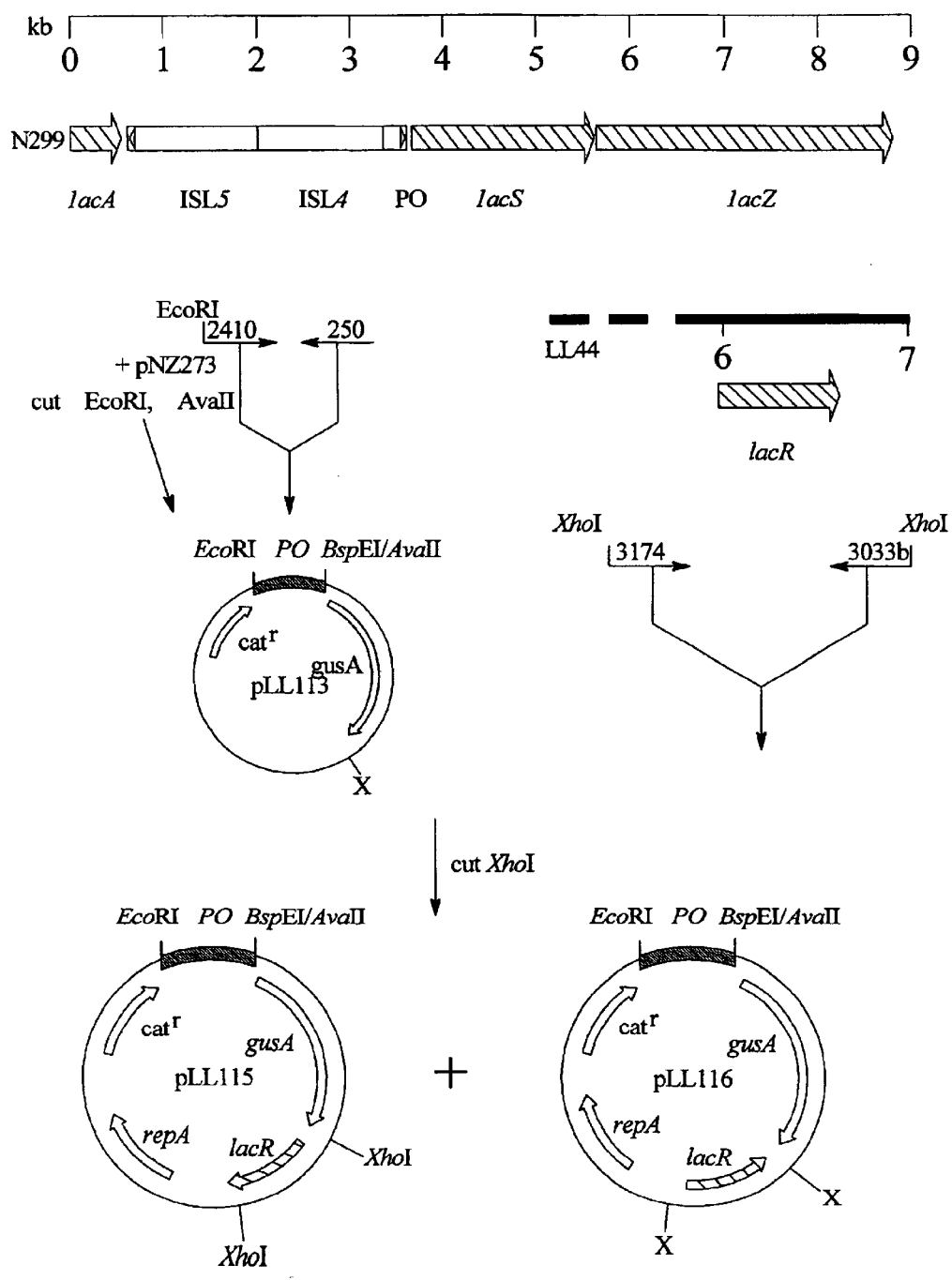

FIG. 8 shows a schematic representation of the construction of pLL113, pLL115 (CNCM I-2090) and pLL116 (CNCM I-2091). Dashed arrows are for the genes of the *L. delbrueckii* lac operon, and open arrows for plasmid genes. The open box containing arrow heads represents the IS-elements. The darkened box is for the promoter region cloned in front of the gusA gene. Plasmids are not drawn to scale. The simple arrows represent the primers used to amplify the cloned regions.

Figure 9:
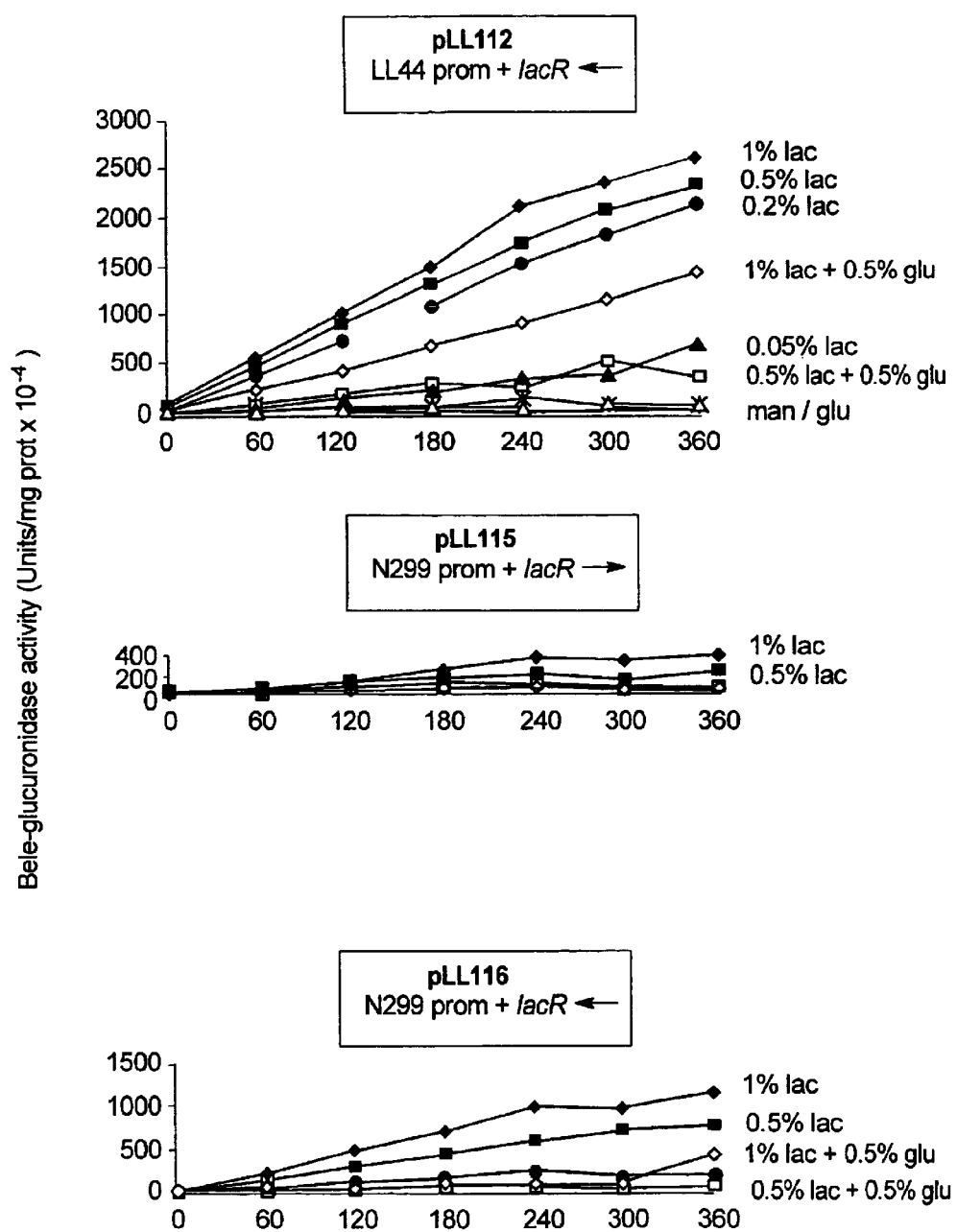

FIG. 9 shows the results of the expression of B (lacta) B-glucuronidase using the constructs of the present invention. Beta-glucuronidase activity (mean of three experiments) of *Lactococcus lactis* MG1363 containing different *Lactobacillus delbrueckii* lac promoter and the lacR gene of LL44. The lacR orientation compared to the gusA gene is represented by an arrow. The medium used was M17 containing: 0.5% mannose, 0.05% lactose, 0.2% lactose, 0.5% lactose, 1.0% lactose, 0.5% glucose, 0.5% glucose+0.5% lactose, and 0.5% glucose+1.0% lactose.

FIG. 10 shows the results of experiments, wherein constructs of the present invention were used to express β-galactosidase in *L. delbrueckii*. Beta-galactosidase activity (mean of three experiments) of *Lactobacillus delbrueckii* subsp. *lactis* LL44 and *L. delbrueckii* subsp. *bulgaricus* N299. The medium used was BHI-broth containing: 0.5% galactose, 0.05% lactose, 0.2% lactose, 0.5% lactose, 1.0% lactose, 0.5% glucose, 0.5% glucose+0.5% lactose, and 0.5% glucose+1.0% lactose. Strain N299 did not grow either in galactose alone or in 0.5% lactose, and the experiment was not realized with these sugars.

The correct regulation of gene transcription and/or translation is a prerequisite for any cellular system to maintain its metabolic and catabolic turn-over and to respond to changes of the environment. In order to better adopt to environmental changes, such as a change of the nutritional source, microorganisms have developed various systems to control gene expression on both, the transcriptional and/or the translational level.

For the gram negative bacterium *Escherichia coli* several of such control systems have been studied. To this end, it has been found that the genes responsible for the catabolism of lactose, that is the genes coding for β-galactosidase (lacZ), lactose permease (lacY) and transacetylase (lacA), respectively, are organized in a particular structural pattern which was termed operon. In this operon the genes coding for the structural polypeptides are located downstream a DNA region coordinating the transcription of said genes (operator) which region is negatively controlled by a repressor protein. The gene coding for the repressor protein is in turn controlled by a different promoter, which allows for a constitutive expression of the repressor.

Under repressive conditions the repressor protein binds to the promoter/operator region thus preventing transcription of the adjacent genes (lacZYA). Yet, in the presence of lactose or allolactose, which represent inducing compounds, the repressor forms a complex with the inducer, which complex has only a limited affinity to the promoter/operator, thus giving way for a transcription of the genes.

The regulation of the lac operon in gram positive bacteria, such as lactic acid bacteria, has been found to be also mediated via a polypeptide acting as a repressor, which is encoded by a gene termed lacR. This gene has been sequenced for *Lactococcus lactis* (van Rooijen et al., J. Biol. Chemistry 265 (1990), 18499–18503) and *Staphylococcus aureus* (Oskouian et al., J. Bacteriol. 169 (1987), 5459–5465). Also in these microorganisms the repressor has a high affinity for the operator and binds to it in the absence of an inducer, resulting in a transcriptional blockade of genes located downstream thereof. In the presence of an inducer molecule, such as lactose or galactose, the repressor is not capable to bind to the operon any more with the all structural genes following the operator region being transcribed together.

In lactic acid bacteria two different systems for the internalisation of lactose into the cells have been reported. Poolman et al. described in J. Bacteriol. 171 (1989), 244–253 a phosphoenolpyruvate dependent phosphotransferase system and a lactose permease system. It is reported that in *Lactobacillus, Streptococcus* and *Leuconostoc* lactose permease acts as a lactose/galactose antiporter system. The microorganisms internalize lactose from the medium as free sugar which is subsequently hydrolyzed to glucose and galactose. Galactose is either converted by the Leloir pathway into glucose-6-phosphate or is released into the medium by the permease.

In J. Bacteriol. 171 (1989), 244–253 and 173 (1991), 1951–1957 the cloning and sequencing of the lactose permease genes (lacS) of *S. thermophilus* and *L. delbrueckii*, respectively, have been reported. The genes were found to be arranged in an operon structure each together with a gene coding for β-galactosidase (lacZ). The gene for β-galactosidase was disclosed for several lactic acid bacteria, such as *S. thermophilus* (Schroeder et al., J. Gen. Microbiol. 137 (1991), 369–380), *L. bulgaricus* (Schmidt et al., J. Bacteriol. 171 (1989), 625–635) and *L. casei*. (Chassy et al., FEMS Microbiol. Rev. 63 (1989), 157–166).

Yet, it has been found that the lac genes may also be subject to catabolite repression. In the presence of particular compounds, such as e.g. glucose, the genes of the lac operon are maintained in a repressed condition. This action is mediated by a cis acting element, that has been first described in *Bacillus subtilis* (Weickert et al., Proc. Natl. Acad. Sci. USA 87 (1990), 6238–6242) and has been termed "Catabolite Responsive Element" (CRE). This element is present in a variety of gene arrangements encoding carbon catabolite enzymes in different gram positive microorganisms and seems to be controlled by the trans acting factors CcpA (Catabolite control protein A) and Hpr. In the presence of glucose both of these proteins bind to the CRE sequence acting as a negative regulation of transcription.

The species *L. delbrueckii* contains mainly two subspecies, *L. lactis* and *L. bulgaricus*, which are defined by several physiological and genetic criteria. One of these criteria concerns the regulation of the lactose (lac) operon expression. In the subspecies *lactis*, the expression is induced by lactose, that is the lac genes are expressed only in the presence of this sugar. In the subspecies *bulgaricus*, which has been selected a long time ago for its ability to ferment milk for yogurt production, the control of the lac genes expression was lost probably due to the constant availability of lactose in milk and the genes are constitutively expressed in the presence or in the absence of lactose.

For the experiments leading to the present invention six representative strains have been chosen to study the regulation of genes via the lac operon. Five strains belong to the subspecies *lactis* and have been termed LL44, LB68, N62 and N141, which are inducible by the presence of lactose, and LB10, that has been classified as belonging to the subspecies *lactis* but with a constitutive expression of the lac operon. The sixth strain, N299, corresponding to ATCC 11842, was chosen as a typical *bulgaicus* strain, with a constitutive expression of the lac genes.

During the analysis of the *lactobacillus* strains the region flanking the lactose (lac) operon was isolated and the following regions could be characterized.

The lac A Gene

During the study of the promoter region of the lac operon, an open reading frame (ORF) of 570 bp was discovered upstream the lacS gene in the same orientation (See FIGS. 2 and 3). This gene was completely sequenced for the *L. delbrueckii* subsp. *lactis* strain LL44 and it encodes a polypeptide, lacA, of 190 amino acid residues. The presence of a putative promoter and a potential ρ-independent-termination signal (stem-loop structure) suggest that this gene does not belong to the lac operon.

The Promoter Region

The region comprised between the end of lacA and the beginning of lacS (lactose permease) was sequenced and showed several attributes specific for a promoter. Two palindromic sequences, called O1 and O2 (FIG. 1-3) were discovered and may serve as operators for the binding of the lac repressor (LacR). The operators of the 6 strains studied (LL44, LB68, N62, N141, LB10 and N299) were sequenced. Several differences were found, which were partly due to the insertion of IS-elements in the O1 inverted repeats and partly due to small nucleotides changes in the sequence (FIG. 1). ISL7 is inserted in N141 exactly at the TGT motif of the 5' end of O1, but restoring the bases TG (FIG. 1). In N299, the *L. delbrueckii* subsp. *bulgaricus* strain, the insertion of ISL5 at the same position destroyed the TGT motif, which might explain the constitutive transcription of adjacent genes.

In lactic acid bacteria, effective repression of transcription is deemed to involve the cooperative binding of LacR to two different operator sequences. In *L. delbrueckii*, a small operator, called O2, was found 4 bp downstream O1. The length of O2 showed considerable variation in length between the 6 strains analysed due to small nucleotide changes in the sequence (FIG. 1). However, no IS-element was found in this operator. The core of both inverted repeats is composed of the nucleotides TGTTTA (SEQ. ID. No. 3) and GTAACA (SEQ. ID. No. 4), except in LL44 where the final A was replaced by G in O2 (SEQ. ID. No. 5).

A sequence of 14 nucleotides homologous to the catabolite responsive element (CRE) (Weickert, supra), was discovered 40 nucleotides upstream the lacS start codon of all the *L. delbrueckii* strains studied (FIG. 2, FIG. 3, 1–14 of SEQ ID No. 8)). Catabolite repression is effective in many bacteria and acts at the level of transcription via negative transcriptional control. It involves a cis-acting element mediating repression of the genes under its control in the presence of glucose. The sequence of these elements is highly conserved among different species and the one of *L. delbrueckii* subsp. *lactis* is highly similar to other elements.

The FIGS. 2 and 3 present a view of the promoter region of the lac operon of 5 of the strains studied. They are considered as representative of the different possible lac operon organisations in the *L. delbrueckii* species. Four inducible *lactis* strains, LL44, LB68, N62 and N141 and one constitutive *bulgaricus* strain, N299 were represented. Strain LB10 was not shown, because its promoter region is identical to N62 except that ISL6 is not present in the lac promoter of this strain. The initiation of transcription in N299 (Leong-Morgenthaler et al., J. Bacteriol. 173 (1991), 1951–1957) falls in the middle of the CRE element, just after the three nucleotides change that were found in the CRE element of this strain (FIGS. 2 and 3).

LL44 was chosen as a reference due to the absence of any IS-element in its lac operon region. In this strain, the lacA gene is followed by the two operators O1 and O2 and the CRE element upstream the lacS gene. In other strains, the presence of IS-elements changed the promoter sequence and particularly the O1 operator sequence.

The lacR Gene

Surprisingly, and in contrast to the gene arrangements of known lac operons, the gene coding for the repressor protein, lacR, was discovered downstream the lacZ gene in *L. delbrueckii* subsp. *lactis* LL44 and LB68, with the result that the repressor is under its own transcriptional control.

The region covering the lacR gene was PCR amplified using the following primers:

CGCCTGGTGATTCAGCC (SEQ ID No. 6)

AGCTTTACGGGGAAGTCGGG (SEQ ID No. 7)

which are located at the end of the β-galactosidase (lacZ) gene for SEQ ID No. 6 and in the Asn-tRNA synthetase (asnA) gene for SEQ ID No. 7.

Sequencing of this region revealed the sequence identified under SEQ ID No. 1, which exhibits an open reading frame of 996 bp in the same orientation as lacZ. The lacR gene is preceded by a ribosome binding site (RBS) and followed by a putative ρ-independent-termination signal (stem-loop structure; position 1149). The putative amino polypeptide derived therefrom is shown under SEQ ID No. 2 (332 amino acid residues).

Computer-assisted analysis of the *L. delbrueckii* lacR gene predicted the protein secondary structure at the beginning of the gene (positions 4 to 23) to be a helix-turn-helix motif which represents the highest homology region with other repressors. This type of protein secondary structure is a common feature for DNA-binding proteins and binds to the operators located in the promoter region.

The lac Operon

The organisation of the lac operon of different *L. delbrueckii* strains is represented in FIG. 5. The lac operon per se is preceded by the thiogalactosyl-transacetylase (lacA) gene, which is followed by a rho-independent termination signal. This gene is followed by the promoter region of the lac operon, which comprises the inverted repeats (operators) involved in the regulation of the gene expression and the CRE sequence. The lac operon is composed of three genes, the permease (lacS), the β-galactosidase (lacZ) and the repressor (lacR). The lacS and lacZ genes are separated by 4 nucleotides, whereas lacR is distant from lacZ by 52 nucleotides.

Five IS-elements have been found in the promoter and the terminator region of the lac operon, which were called ISL3, ISL4, ISL5, ISL6 and ISL7. One of these Elements, ISL3, has been described in Germond et al, Mol. Gen. Genet. 248 (1995), 407–416.

The lactose permease (lacS), the β-galactosidase (lacZ) and the repressor (lacR) constitute the lac operon per se. The three genes are linked together as a lacSZR operon in *L. delbrueckii* subsp. *lactis* without any promoter in between. This gene arrangement is not a common feature for regulated operons, as the lacR gene is normally not a part of the operon.

The lac operon of *L. delbrueckii* is furthermore induced exclusively by lactose, and, as part of the operon, the repressor is deemed to be increasingly produced under inducible conditions. In *L. delbrueckii* subsp. *bulgaricus*, the typical yogurt strain, the lacR gene was inactivated by small nucleotides insertions and deletions in the sequence resulting in the constitutive phenotype of this subspecies.

In *L. delbrueckii* subsp. *lactis*, the repressor is able to bind to the promoter region which is located upstream the lacS gene. This region contains two inverted repeated sequences, O1 and O2, which seem to assist in the binding. The presence of two operators stabilizes the complex with the repressor in vitro, which occurs via DNA looping between the operator and the different subunits of the repressor.

The degree of repression depends from the position of the operators in the promoter region. A repressor bound between the −10 element and the start codon suffers in competition with the polymerase since this molecule can form a complex with the −35 element, whereas an operator located upstream the −35 element is not very effective since it allows the polymerase to access the −10 element and the initiation site. An operator located in the spacer region ensures a tighter control of the operon. The O1 operator of *L. delbrueckii* is located upstream the −35 element, whereas the O2 operator is located in the spacer region. This operator is very variable in length, ranging from 11 nucleotides in LL44 to 22 in N299.

To study the functionality of the promoter/repressor system in vitro, the promoters of the inducible strain LL44 and constitutive strain N299 were cloned in front of reporter genes, e.g. chloramphenicol acetyltransferase or β-glucuronidase, in the presence or absence of the repressor gene. Different expression systems were tried in *E. coli* and *Lactococcus lactis*.

Induction of β-glucuronidase production showed considerable differences between the different promoters associated to LL44 lacR. The plasmid carrying the LL44 promoter (pLL112) was fully induced by 1.0% lactose up to levels of 250 mU/mg protein, whereas plasmids carrying the N299 promoter (pLL116) reached about 100 mU/mg protein when the lacR gene was in the reverse orientation as the gusA gene. When the lacR gene was introduced in the same orientation as the gusA gene (pLL115), levels of induction dropped to around 40 mU/mg protein. This may be explained by the absence of a promoter in front of lacR and its control either by the N299 strong lac promoter when it is in the sense of the gusA gene or by a weak promoter which must be located on pNZ272 when it is orientated antisense. It was also not possible to obtain the lacR gene in the same sense than gusA with the LL44 promoter. Production of GusA also showed that all plasmids were subjected to glucose catabolite repression due to the presence of a CRE sequence in the promoter of *L. delbrueckii*. The CRE of N299 is partly disrupted and the repression observed with this promoter is weaker than with LL44.

Measurements of the β-galactosidase activity in vivo revealed that the *L. delbrueckii* strains were almost not subjected to glucose catabolite repression. The β-galactosidase activity also confirmed the inducible characteristics of the *L. delbrueckii* subsp. *lactis* strains and the constitutivity of the *bulgaricus* strains. Indeed, LL44, LB68, N62 and N141 were not induced in the presence of glucose as sole carbon source, whereas in N299 β-galactosidase activity was also high in the glucose medium. The inducible characteristic of an operon allows the strain to quickly switch from metabolizing one substrate to another.

Thus, according to the present invention the transcription and/or expression of homologous and/or heterologous genes in bacteria may be suitably obtained by preparing the construct p/o-(A)$_n$-R$_y$ or p/o-R$_y$-(A)$_n$ as illustrated above and introducing said construct into the bacterium.

According to the present invention it is now possible to control the transcription and/or expression of a specific gene polypeptide by adjusting the content of glucose and/or lactose, respectively, in the culture medium. As an example, the bacterium may be grown in a medium lacking lactose to a desired degree and in a next step may then be transferred to a medium containing lactose or lactose is simply added to the medium. Only at his stage the repressive activity of the construct on the transcription and/or expression of the gene of interest will be relieved and the gene product will be produced.

In order to assist the inductive activity of the construct the gene for the lactose permease may be one of the polypeptides designated "A". To this end, if an amount of lactose enters the bacterial cell the genes following the promoter described here are transcribed with one of the polypeptides to be expressed thereby being lactose permease, which actively transfers additional lactose into the cell.

Further, it may well be suitable to delete the region harboring the catabolite responsive element, so that the construct is not subject to carbon repression.

The following examples illustrate the invention without limiting the scope of the appended claims.

EXAMPLE 1

Bacterial Strains and Growth Conditions

Lactobacilli were grown in Difco *Lactobacillus* MRS-broth (DeMan et al., J. Appl. Bacteriol. 23 (1960), 130–135) or in Oxoid BHI-broth. *Lactococci* strains were cultivated in Difco M17-broth (Terzaghi et al., Appl. Microbiol. 29 (1975), 807–813) supplemented with 0.5% glucose (GM17). *E. coli* was grown in YT-broth 2× prepared according to Maniatis et al., Molecular cloning: A Laboratory Manual, 2nd ed. Cold Spring Harbor Laboratory, Cold Spring Harbor, N.Y. (1989). All strains were stored at −80° C. in their respective media containing 10% glycerol ten times concentrated.

For plasmid selection and maintenance in *Escherichia coli*, ampicillin (100 μg/ml), chloramphenicol (30 μg/ml), or kanamycin (50 μg/ml) were added to the growth medium (ampicillin and kanamycin obtained from Sigma, chloramphenicol from Boehringer Mannheim). For plasmid selection and maintenance in *Lactococcus lactis* MG1363, chloramphenicol at 12 μg/ml was added to the growth medium.

Chromosomal and Plasmid DNA Purification

*Lactobacilli* DNA was prepared according to Delley et al., Appl. Environ. Microbiol. 56 (1990), 1967–1970. Plasmid DNA from *E. coli* was purified by the alkali lysis method (Maniatis, supra). *Lactococcus* plasmid DNA was prepared following the same procedure, except that the cultures were first incubated 30 min at 37° C. in TE (10 mM Tris-HCl, pH 8.0; 1 mM EDTA) containing 10 mg/ml lysozyme (all chemicals obtained from SIGMA).

DNA Manipulations and Bacterial Transformations

Agarose gel electrophoresis, restriction enzyme digestions, ligations and transformations in *E. coli* were performed according to standard procedures (Maniatis, supra). When necessary, the digested DNA was blunt-ended with $T_4$ DNA polymerase (Boehringer-Mannheim) directly in the digestion mixture for 5 min at 37° C.

The different *L. delbrueckii* operators were cloned into plasmid pKK232-8 (Ap$^r$, Cam$^r$, contains a promoterless chloramphenicol acetyltranferase (cat) gene, *E. coli* vector, Pharmacia) and transformed in *E. coli* SURE (obtained from STRATAGENE). Transformants were selected on YT-agar plates containing 30 μg/ml chloramphenicol. The LL44 lacR gene was cloned into plasmid pKK223-3 (Ap$^r$, contains a strong tac promoter, Pharmacia) and transformed in *E. coli* SURE. Transformants were selected on YT-agar plates containing 100 μg/ml ampicillin. For lacR overexpression, 2 mM isopropyl-β-D-thioga-lactoside (IPTG) was added to the culture and cells were allowed to grow for an additional 4–5 hours at 37° C. Cultures were centrifuged and the pellets were resuspended in 0.1 M Hepes, sonicated and centrifuged. Supernatants were applied to a SDS/PAGE gel (Laemmli, Nature 227 (1970), 680–685).

When the lacR gene was cloned into plasmid pET11c (obtained from STRATAGENE), plasmids were transformed in *E. coli* BL21 (STRATAGENE). Transformants were selected on YT-agar plates containing 100 μg/ml ampicillin, and lacR was overexpressed as described above in the presence of 1 mM IPTG. The lacR gene was finally cloned into plasmid pACYC177 (New England Biolabs) into the PstI site of the ampicillin gene and transformed in *E. coli* XL1-Blue (SRATAGENE). Transformants were selected on YT-agar plates containing 50 μg/ml kanamycin. Plasmid pACYC177 containing the lacR gene was cotransformed with the pKK232-8 plasmids containing the different operators in *E. coli* XL1-Blue. Transformants were selected on 100 μg/ml ampicillin for the presence of pKK232-8 and 50 μg/ml of kanamycin for the presence of pACYC177.

Competent cells and transformations of *Lactococcus lactis* MG 1363 were realized according to Holo et al. Appl. Eviron. Microbiol. 55 (1989), 3119–3123. Cells were grown in GM17-broth containing 500 mM sucrose and 3% glycine to an $OD_{600}$ of 0.2–0.3, centrifuged and washed several times in a solution containing 500 mM sucrose and 10% glycerol. Competent cells were stored 100× concentrated at −80° C. in the same solution until use.

Cells (40 μl) were mixed with 5 μl of plasmid DNA and electrotransformed at 2.0 kV, 25 μF and 200 Ω. Cells were resuspended in GM17-broth containing 20 mM $MgCl_2$ and 2 mM $CaCl_2$ and expressed for 90 min at 30° C. Cells were then plated on GM17-agar containing 12 μg/ml of chloramphenicol. When the different *L. delbrueckii* promoters were cloned upstream the GUS gene, 50 μg/ml of X-glu (5-bromo-4-chloro-3-indolyl-β-D-glucuronide) (Amresco) was added to the GM17-agar plates to select for blue colonies.

DNA Amplification and Sequencing

DNA amplification was done by polymerase chain reaction (PCR) in the presence of 0.2 mM of each dNTPs, 1 μM of each oligonucleotide primers, the appropriate buffer and the Taq polymerase (Gold polymerase, Perkin-Elmer) under the following conditions: 1 min at 94° C.-2 min at 55° C. and 3 min 30 at 72° C. for 35 cycles. Custom made oligonucleotide primers were used. DNA sequences were determined directly by PCR using the VISTRA Thermo sequenase sequencing kit (Amersham) (Sanger et al., Proc. Natl. Acad. Sci. USA 74 (1977), 5463–5467) and then analysed with the help of the University of Wisconsin, USA, Genetics Computer Group (GCG) computer software package (Devereux, Nucleic Acids. Res. 12 (1984), 387–395).

Isolation of Spontaneous Repressor Negative LL44 Mutants

The *L. delbrueckii* subsp. *lactis* strain LL44 was isolated on MRS-agar containing glucose and 200 μg/ml X-gal (5-bromo-4-chloro-3-indolyl-β-D-galactopyranoside) (Sigma) to check the inducible state of its lac operon. One white colony was further incubated overnight at 42° C. in MRS-broth containing 10% lactose. The culture was stored refrigerated for 24 hours and then subcultured in MRS-broth containing 10% lactose for 7 h at 42° C. This culture was diluted and plated on Oxoid Reinforced Clostridial Medium (RCM) agar containing only glucose and 200 μg/ml X-gal to select for a blue lac constitutive mutant. Plates were incubated for 72 h at 40° C. under microaerophilic conditions (BBL, microaerophilic system No. 71034). A blue colony was obtained, further cultivated and stored in MRS-broth as described above.

Chloramphenicol Acetyltransferase Assay (Shaw, Methods Enzymol. 43 (1975), 737–755.

Cells were grown overnight in YT-broth 2× containing the necessary antibiotics (see DNA manipulations and bacterial transformations) at 37° C. under shaking. 10 ml of fresh YT-broth containing either 0.5% lactose or 0.5% glucose was inoculated with 1% of the overnight culture. Kanamycin (50 μg/ml) and/or ampicillin (100 μg/ml) were used as antibiotics. Cells were incubated for 3 hours at 37° C., centrifuged and the pellet was resuspended in 2 ml Hepes 0.1 M. The suspension was sonicated for 30 sec, spun down and the supernatant was mixed with 1 volume of buffer 2× concentrated (200 mM Tris-HCl, [pH 8.0]-0.2 mM Acetyl CoA-0.8 mg/ml DTNB) and chloramphenicol was added at a final concentration of 0.1 mM. The mixture was incubated at 37° C. for 4 min and the OD red at 412 nm.

In a second cycle of experiments, the YT-broth was replaced by a solution containing: ⅕ vol M9-salts 5× ($Na_2HPO_4 \cdot 7H_2O$, 450 mM-$KH_2PO_4$, 110 mM-NaCl, 45 mM-$NH_4Cl$, 93 mM), 0.5% glucose or lactose, 1 mM $CaCl_2$, 20 mM $MgCl_2$ and 10 mM thiamine. The rest of the assay was realised as described above.

Determination of β-Glucuronidase Activity (Modified from Bergmeyer, Methods of Enzymatic Analysis 2 1983, 206–209)

Starters of transformed *Lactococcus lactis* were prepared by incubating the bacteria overnight at 30° C. in M17-broth containing 0.5% mannose and 12 μg/ml chloramphenicol. Ten ml of M17 containing different sugars were inoculated at 2% with the overnight culture and incubated at 30° C. to an $OD_{660}$ of about 1.0. Following centrifugation, cells were stored at −20° C. until use. For the assay, they were resuspended in 2 ml of distilled water containing 0.1% Triton X100, incubated 30 min at room temperature and collected by centrifugation. Cells were then resuspended in 2 ml of GUS buffer (50 mM $NaHPO_4$ [pH 7.0], 10 mM β-mercaptoethanol, 1 mM EDTA, 0.1% Triton X100) containing 50 μg/ml of para-nitrophenyl-β-D-glucuronide (Clonetech). After 1 hour incubation at 37° C., 500 μl were mixed with 500 μl of stop solution (2 mM $Na_2CO_3$) Centrifugation was followed by absorbance measurement at 415 nm. β-glucuronidase activity was calculated by using the equation:

$$U/mg\ prot. = OD_{415} \times dilution\ factor/18 \times t \times mg\ prot./ml$$

wherein t is the reaction time, 18 the millimolar extinction coefficient of the para-nitrophenol and 0.4 the dilution factor.

The protein content of the culture was determined as described by Bradford. Anal. Biochem. 12 (1976), 248–254, using the Bio-Rad protein assay with bovine serum albumin as standard. Samples of 0.1 ml of the culture were mixed with 5 ml Bio-Rad dye reagent (diluted 1:4 with distilled water). After incubation for 5 min. the absorbance was red at 550 nm.

For the β-glucuronidase induction, fresh M17-broth containing 0.5% mannose and 12 μg/ml chloramphenicol was inoculated at 2% with the starter cultures and incubated at 30° C. to an $OD_{660}$ of about 0.2. The cultures were split and the different sugars added. Cultures were further grown at 30° C. until the $OD_{660}$ reached 1.0. β-glucuronidase activity was measured as described above at 60 min intervals.

Determination of β-Galactosidase Activity (Modified from Bergmeyer, supra)

Starters of *L. delbrueckii* were prepared by incubating bacteria overnight in MRS-broth at 42° C. 10 ml of BHI containing different sugars (table I) were inoculated at 2% with the overnight culture and incubated at 42° C. to an $OD_{600}$ of about 1.0. For the *Lactobacillus delbrueckii* subsp. *lactis* strain N141, galactose was replaced by mannose (as galactose induced the lac operon). Following centrifugation, cells were stored at −20° C. until use. For the assay, pellets were resuspended in 2 ml of distilled water containing 0.1% Triton X100, incubated at room temperature for 30 min, and collected by centrifugation. Cells were resuspended in 2 ml of Z buffer (0.06 M $Na_2PO_4$; 0.04 M $NaH_2PO_4 \cdot 7H_2O$; 0.01 M KCl; 0.001 M $MgSO_4 \cdot 7H_2O$; 0.05 M β-mercaptoethanol [pH 7.0]) (Miller, Experiments in Molecular Genetics, Cold Spring Harbor Laboratory, Cold Spring Harbor, N.Y., 1972), diluted 10 times in the same buffer containing 50 μg/ml ortho-nitrophenyl-β-D-galactopyranoside (ONPG). After 30 min incubation at 42° C., 200 μl were mixed with 800 μl of stop solution (400 mM $Na_2CO_3$; 50 mM EDTA) Centrifugation was followed by absorbance measurement at 420 nm. β-galactosidase activity was calculated by using the equation:

$$U/OD_{600} = OD_{420} \times dilution\ factor/3.5 \times t \times OD_{600},$$

wherein t is the reaction time, 3.5 the millimolar extinction coefficient of the ortho-nitrophenol and 10 the dilution factor.

For the induction of β-galactosidase, fresh BHI-broth containing 0.5% galactose was inoculated with the starter cultures and incubated at 42° C. to an $OD_{600}$ of about 0.2. The cultures were split and the different sugars were added. Cultures were further grown at 42° C. to an $OD_{600}$ of about 1.0. β-galactosidase activity was measured as described above at 15 min intervals.

EXAMPLE 2

Expression of the *L. delbrueckii* LL44 lacR Gene in *E. coli*

The lac repressor (lacR) gene of *L. delbrueckii* strain LL44 was tentatively expressed in *E. coli*. It was first PCR amplified using the following primers

```
        Pst I                         SEQ ID No.10
ATATTACTGCAGAGTAAAAGCGAGT

Hind III                      SEQ ID No. 11
ATAAATAAGCTTACAGAATGCAGCC
``` which contain a PstI and a HindIII site, respectively. The fragment was cloned in the corresponding sites behind the strong tac promoter of pKK223-3, a high copy-number plasmid, and transformed in *E. coli*. The presence of lacR in the resulting clone, termed pLL56, was verified by sequencing. Upon 2 mM IPTG induction an expression of the gene could be obtained.

EXAMPLE 3

Cloning of the *L. delbrueckii* lac Promoter in Front of the Chloramphenicol Acetyltransferase Gene in *Escherichia coli*

The lac promoters of *L. delbrueckii* LL44, N141 and N299 were tentatively cloned in front of an *E. coli* reporter gene, the chloramphenicol acetyltransferase (cat) gene. They were PCR amplified using the following primers

```
        Eco RI
ATATTAGAATTCAGTGACTTAAACTGG       SEQ ID No. 12

Eco RI
ATATTAGAATTCAGTACTTTGACACCG       SEQ ID No. 13

Eco RI
ATATTAGAATTCAAGAGGCTATATCGC       SEQ ID No. 14

GGTTAATGCCGCCAAGT                 SEQ ID No. 15
``` which contain an EcoRI site and primer 250 which is located in the lacS gene. The amplified fragments were digested with EcoRI and BspEI, which cleave in the primer sequence and 170 bp downstream the start condon of lacS. Restriction sites were filled with $T_4$ DNA polymerase, cloned in front of the promoterless cat gene of pKK232-8 digested with SmaI and transformed in *E. coli*. Chloramphenicol resistant clones were obtained for the three *lactobacilli* lac promoters, which indicates that the lac promoters of *L. delbrueckii* are active in *E. coli*. They were called pLL55 for N299, pLL57 for N141 and pLL58 for LL44 and all the constructs were verified by sequencing.

EXAMPLE 4

Control of the *L. delbrueckii* lac Promoters by the LL44 lacR Gene in *E. coli*

To test if the *L. delbrueckii* lac promoters could be controlled by the LL44 lacR in *E. coli*, plasmids pLL55, pLL57 and pLL58 were cotransformed with a low copy number plasmid containing the LL44 lacR gene under the control of the promoter of *E. coli* lac repressor (lacI). To obtain this construct, the two DNA fragments were linked by the Gene Splicing by Overlap Extension (gene SOEing) method (Horton R., Molecular Biotechnology 3 (1995), 93–99).

The promoter of lacI was first amplified from pET11c using the following primers

```
        Pst I
ATAAATCTGCAGTGGGTATGGTGGC           SEQ ID No. 16

GATCGTTGCCACATTCACCACC              SEQ ID No. 17
```

The primer SEQ ID No. 18 is composed of a sequence of the lacI promoter and of the *L. delbrueckii* 5' end of lacR. The complete lacR gene was then PCR amplified using the following primers

```
GGTGAATGTGGCAACGATCAG               SEQ ID No. 18

PstI
ATATTACTGCAGACAGAATGCAGCC           SEQ ID No. 19
```

Both PCRs were purified, mixed and reamplified with primers SEQ ID No. 16 and SEQ ID No. 19, linking the lacI promoter and the LL44 lacR gene. Additionally, the ATG start codon of the lacR gene was replaced by GTG as in lacI (FIG. 6). The whole construct was cloned in the PstI site of the low copy number plasmid pACYC177 (New England Biolabs) digested with PstI and resulted after transformation in plasmid pLL62 (FIG. 6). The presence of the modified lacR gene in pLL62 was confirmed by digestions and PCR amplifications.

This plasmid was cotransformed with pLL55, pLL57 and pLL58 in *E. coli* resulting in strains LZL63, LZL64 and LZL65 (Table I) respectively. The resulting strains contained the different *L. delbrueckii* promoters together with the LL44 lacR gene. Regulation of the promoters was tested following the chloramphenicol acetyltransferase assay of Shaw, supra in the presence of lactose or glucose. The results showed that after 4 min incubation at 37° C., strains containing the different promoters were fully induced in YT medium or in a minimal medium based on M9-salts in the presence or in the absence of lacR as shown in the table below:

TABLE I chloramphenicol acetyltransferase assay (Shaw, 1975)

| Plasmid | Sugar | YT-broth $OD_{415}$ | Sugar | M9-salts $OD_{415}$ |
|---|---|---|---|---|
| pKK232-8 | glucose | 1.8 | | |
| pKK232-8 | lactose | 1.9 | | |
| LZL63 | glucose | 2.6 | glucose | 0.7 |
| N299 prom. (pLL55) + lacR (pLL62) | lactose | 2.5 | lactose | 0.9 |
| LZL64 | glucose | 2.5 | glucose | 0.8 |
| N141 prom. (pLL57) + lacR (pLL62) | lactose | 0.4 | lactose | 1.2 |
| LZL65 | glucose | 1.2 | glucose | 1.3 |
| LL44 prom. (pLL58) + lacR (pLL62) | lactose | 1.1 | lactose | 1.0 |

The $OD_{415}$ was red following 4 min incubation at 37° C.

The same results were found for the Gram-positive bacterium *Staphylococcus aureus*, where the lac promoter was functional in *E. coli* but the lacR gene not. One possible explanation is that an additional factor, present only in Gram-positive bacteria, is necessary for proper repressor function.

EXAMPLE 5

Cloning of the *L. delbrueckii* lac Promoters in Front of the β-Glucuronidase Gene in *Lactococcus lactis*

The lac promoters of LL44 (inducible) and N299 (constitutive) were cloned in front of a reporter gene, the β-glucuronidase (gusA) gene. They were PCR amplified using primers SEQ ID No. 12 and No. 14, respectively, both containing an EcoRI site and primer SEQ ID No. 15 which is located in the lacS gene. The amplified fragments were digested with BspEI, located 170 bp downstream the lacS start codon, filled with $T_4$ DNA polymerase, and digested with EcoRI. Fragments were then cloned in front of the promoterless gusA gene of pNZ272 (Platteeuw et al, Appl. Env. Microb. 60 (1994), 587–593) digested with AvaII (refilled with $T_4$ DNA polymerase) and EcoRI. The resulting plasmids, pLL110 for LL44 and pLL113 for N299, were transformed in *Lc. lactis* (MG1363, plasmid free) (FIGS. 7 and 8).

Chloramphenicol resistant clones were screened in the presence of 5-bromo-4-chloro-3-indolyl-β-D-glucuronide (X-glu), which is cleaved by the glucuronidase generating a blue color due to the liberation of the indol group of X-glu. Both plasmids were able to express β-glucuronidase, indicating that the lac promoter of *L. delbrueckii* is functional in *Lc. lactis*. The presence of the different promoters was checked by sequencing.

EXAMPLE 6

Cloning of the *L. delbrueckii* lacR Gene Behind the β-Glucuronidase Gene in *Lactococcus lactis*

To test if the lac promoters can be controlled by the *L. delbrueckii* lac repressor, the lacR gene of LL44 was cloned on plasmids pLL110 and pLL113. The lacR gene was PCR amplified using the following oligonucleotides:

```
    Xho I
ATAAATCTCGAGTGGTGATTCAGCC           SEQ ID No. 20

Xho I
ATATTACTCGAGACAGAATGCAGCC           SEQ ID No. 21
``` both containing a XhoI site. The primers were chosen to induce flanking regions of the gene. That is the oligonucleotide SEQ ID No. 20 is located 80 bp upstream the lacR start codon in the lacZ gene and the oligonucleotide SEQ ID No. 21 70 bp downstream the lacR stop codon, in the Asn-tRNA synthetase (asnA) gene. The fragment was cleaved with XhoI and cloned in the same site downstream the gusA gene of pLL110 and pLL113. With pLL110 containing the LL44 lac promoter, one clone (pLL112) was obtained with a lacR gene inserted in the opposite (rev) orientation as the gusA gene (FIG. 7). With pLL113 containing the N299 promoter, the lacR gene could be cloned in both orientations, pLL115 in the same (for) and pLL116 in the reverse (rev) orientation as the gusA gene (FIG. 8). The mutated lac repressor ((X)lacR) gene of LZL102 was PCR amplified and cloned as described above for LL44, resulting in plasmids pLL111 with the lac promoter of LL44 and pLL114 with the promoter of N299, both in the same orientation as gusA.

EXAMPLE 7

Control of the β-Glucuronidase Activity in *Lactococcus lactis*

The different constructs containing the *L. delbrueckii* lac promoters and repressors were studied by growing the transformed *Lc. lactis* in the presence of mannose. This sugar was shown to have no influence on the lactose metabolism of *Lactococcus*, as compared to saccharose and cellobiose. Exponentially growing cells were diluted into fresh media containing different concentrations of lactose and glucose, grown and harvested. β-glucuronidase (GusA) activity was measured from permeabilized cells in the presence of p-nitrophenol-β-D-glucuronide, which is cleaved by GusA, liberating para-nitrophenol staining the solution in yellow. The results of these experiments are shown in FIG. 9.

EXAMPLE 8
Regulation of the lac Promoter of *L. delbrueckii* subsp. *lactis* LL44

The promoter of LL44 (pLL110) was functional in *Lc. lactis* resulting in the production of β-glucuronidase in the presence of lactose or mannose. When glucose was added to the medium with or without lactose, a five to seven fold reduction in GusA activity was observed. This indicates that the glucose catabolite repression is efficient in the system.

pLL116, rev), almost no GusA activity was detected in the presence of mannose. This result indicates that the so called "constitutive" promoter of *L. delbrueckii* subsp. *bulgaricus* is in fact repressed by the *L. delbrueckii* lac repressor. In addition, increasing concentrations of lactose induced increasing production of GusA activity. Nevertheless, the production even at 1% lactose with the repressor in the reverse orientation (pLL116) reached only half of that obtained in the absence of repressor. The N299 is not only regulated by the repressor, but more tightly than that of LL44.

Finally in the presence of the mutated repressor (pLL114), the GusA activity was 3 to 4 times lower than in the absence of any repressor. On this promoter the ⊗lacR seems to have a general inhibiting activity as a low activity is observed with or without lactose.

EXAMPLE 10
Lactose Induction of *L. delbrueckii* Promoters in *Lactococcus lactis*

TABLE II

Expression of the gusA gene fused to the *L. delbrueckii* lac promotor in *Lactococcus lactis* MG1363 grown in M7

| | Beta-glucuronidase activity (U/mg prot. × $10^{-4}$)$^\alpha$ | | | | | | | | |
|---|---|---|---|---|---|---|---|---|---|
| | *L. lactis* LL44 promoter | | | | *L. bulgaricus* N299 promoter | | | | |
| Sugar added | pLL110 — | pLL111 + ⊗lacR$^b$ | pLL112 + lacR | pLL113 — ← | | pLL114 + ⊗lacR | pLL115 + lacR | pLL116 + lacR | → ← |
| 0.5% mannose | 20.1 ± 8.0 | 35.7 ± 9.8 | 0.5 ± 0.5 | 35.8 ± 0.5 | | 9.9 ± 0.6 | 1.1 ± 1.2 | 0.7 ± 0.7 | |
| 0.05% lactose | 15.6 ± 4.4 | 35.8 ± 7.1 | 3.4 ± 1.1 | 32.0 ± 4.1 | | 10.5 ± 2.2 | 0.7 ± 0.7 | 0.7 ± 0.8 | |
| 0.2% lactose | 15.1 ± 4.5 | 34.1 ± 7.5 | 20.7 ± 13.4 | 34.4 ± 7.2 | | 8.2 ± 1.6 | 0.9 ± 1.2 | 0.3 ± 0.1 | |
| 0.5% lactose | 20.1 ± 12.6 | 37.0 ± 7.8 | 27.1 ± 7.5 | 34.1 ± 9.4 | | 8.5 ± 1.1 | 1.5 ± 1.0 | 11.1 ± 1.3 | |
| 1.0% lactose | 15.3 ± 6.0 | 29.7 ± 1.3 | 23.8 ± 8.6 | 33.7 ± 7.0 | | 8.7 ± 0.8 | 3.2 ± 0.5 | 12.8 ± 4.8 | |
| 0.5% glucose | 5.1 ± 3.7 | 34.6 ± 9.1 | 0.5 ± 0.2 | 22.3 ± 2.0 | | 5.6 ± 1.0 | 0.7 ± 0.8 | 0.6 ± 0.6 | |
| 0.5% glucose + 0.5% lactose | 3.5 ± 1.4 | 32.5 ± 4.9 | 3.3 ± 1.6 | 28.0 ± 7.6 | | 6.0 ± 0.8 | 0.6 ± 0.6 | 2.0 ± 0.7 | |
| 0.5% glucose + 1.0% lactose | 3.7 ± 0.9 | 38.7 ± 12.0 | 4.8 ± 2.2 | 22.5 ± 6.6 | | 4.7 ± 1.0 | 0.6 ± 0.2 | 4.0 ± 1.2 | |

In the presence of the repressor gene (pLL112), GusA activities were similar to those observed with pLL110 when lactose (0.2 to 1%) was added. Almost no activity was observed with mannose (Table 2) indicating that the repressor is expressed in *Lc. lactis* and can bind to the lac promoter. Galactose, which is a common inducer of the lac system showed no induction of the system. Plasmid pLL112 was also subjected to the glucose catabolite repression, with a five to nine fold reduction in activity.

Surprising results were obtained with pLL111, the plasmid which contains the ⊗lacR of LZL1012 and the LL44 lac promoter. GusA activities were twice higher than with the lac promoter alone even in the presence of glucose (Table II). The mutated repressor, with half of the protein translated, seems to play the role of an enhancer.

EXAMPLE 9
Regulation of the lac Promoter of *L. delbrueckii* subsp. *bulgaricus* N299

The lac promoter of N299 (pLL113) induced production of GusA activity, almost twice as much as that produced by the promoter of LL44 (Table II, above). The N299 promoter is thus also functional in *Lc. lactis*. In the presence of glucose, only a relatively weak repression was observed, which could be explained by a different sequence of the CRE motif.

In the presence of the LL44 lacR gene, cloned in both orientations behind the gusA gene (pLL115, for and The GusA activity was measured at several times during exponential growth of *Lc. lactis* containing the lac promoters of LL44 and N299 and the lacR gene of LL44 (pLL112, pLL115 and pLL116) in the presence of different concentrations of lactose and glucose (FIG. 9). The lac promoter of LL44 was maximally induced with 1% lactose and clearly subjected to glucose catabolite repression, i.e. 0.5% glucose in addition to lactose reduced this activity by half. As expected, mannose and glucose alone generated no GusA activity. Plasmids containing the N299 lac promoter (pLL115, for and pLL116, rev) are hardly inducible and are completely inhibited by glucose. Plasmid pLL115, having the repressor gene in the same orientation as gusA, resulted in the lowest lactose induction. In this case, it can be postulated that the repressor is produced in large amounts under the control of the *L. delbrueckii* lac promoter whereas in pLL116, it must be under the control of a weak promoter present on pNZ273 and is thus produced in smaller amounts.

EXAMPLE 11
β-Galactosidase Activity in *Lactobacillus delbrueckii*

The relation between the lac promoter and the lac repressor were studied in situ. β-galactosidase (β-gal) activity was measured in different *L. delbrueckii* strains in BHI-broth containing different sugars. The *L. delbrueckii* subsp. *lactis* strains tested showed no or low β-gal activity in the presence of mannose/galactose or glucose.

TABLE III

Expression of the lacZ gene in different strains of
Lactobacillus delbrueckii grown in BHI
Beta-galactosidase activity (mU/OD600)

| Sugar added | LL44 | LZL102 | LB68 | N62 | N141 | LB10 | N299 |
|---|---|---|---|---|---|---|---|
| 0.50% galactose | 2.4/1.8 | 6.4/9.5 | 2.4/2.0 | 0.0/0.0 | 0.6/0.5[a] | 15.3/12.6 | 7.9/14.9 |
| 0.02% lactose | 14.1/17.5 | 12.1/9.5 | 21.2/20.6 | 11.5/9.5 | 13.5/9.7 | 18.0/12.1 | 14.3/10.6 |
| 0.05% lactose | 11.4/13.9 | 7.4/9.5 | 24.3/20.6 | 11.6/9.1 | 11.0/10.9 | 16.9/8.6 | 9.5/18.1. |
| 0.2% lactose | 10.1/12.3 | 11.6/9.5 | 14.1/20.3 | 8.8/8.1 | 7.6/8.3 | 10.2/7.4 | 23.8/23.8 |
| 0.5% lactose | 19.0/8.7 | 10.6/9.5 | 20.4/16.5 | 15.4/12.4 | 9.8/5.5 | 12.8/11.1 | 29.0 |
| 0.5% lactose | 0.9/0.6 | 14.7/9.5 | 3.2/1.9 | 0.0/0.0 | 2.5/2.2 | 12.6/7.8 | 39.7/15.5 |
| 0.5% glucose + 0.5% lactose | 15.9/7.1 | 11.7/9.5 | 15.6/16.8 | 17.9/33.1 | 6.3/5.4 | 8.0/7.6 | 28.6/31.7 |
| 0.5% lactose + 1.0% lactose | 7.7/6.7 | 16.6/9.5 | 15.4/15.5 | 14.9/13.1 | 9.3/7.0 | 12.0/10.3 | 22.0/23.8 |

[a]: galactose was replaced by mannose

At all concentrations of lactose tested (0.02 to 0.5%), the β-gal activity was in the same range, indicating that very low concentration of lactose is able to fully induce the expression of the lac operon. In the presence of lactose and glucose, strains were not subjected to catabolite repression and even a stimulation of β-gal activity was found for N62 (Table 3, above). The constitutive *L. delbrueckii* subsp. *bulgaricus* N299 showed the same β-gal activity with all sugars used even in the presence of glucose. Two mutants of *L. delbrueckii* subsp. *lactis*, LB10 and LZL102, were also analysed. LZL102, the spontaneous mutant of LL44, produces a truncated repressor and LB10 produces no peptide at all. In both cases, strains were constitutive with equal amounts of β-gal produced with galactose, lactose or glucose.

EXAMPLE 12

Lactose Induction of the lac Promoters in *Lactobacillus delbrueckii*

The β-gal induction was measured at several times during exponential growth of the *L. delbrueckii* subsp. *lactis* strain LL44 and the *bulgaricus* strain N299. The maximum level of activity was reached in both strains after 15 min incubation (FIG. 10). For LL44, no β-gal activity was detected with galactose or glucose, whereas full induction was obtained with all lactose concentrations. The enzymatic activity was slightly reduced in the presence of glucose, i.e. a full activity was only reached after 60 min. For N299, all sugars resulted in the same induction with no glucose catabolite repression.

What is claimed is:

1. An isolated DNA expression construct comprising a DNA sequence represented by a general formula selected from the group consisting of:

$$p/o\text{-}(A)_n\text{-}R_y, \text{ and}$$

$$p/o\text{-}R_y\text{-}(A)_n$$

wherein
  i) p/o is a *Lactobacillus delbrueckii* subsp. *lactis* promoter that is SEQ ID NO: 9,
  ii) A is a heterologous gene encoding a polypeptide of interest; and
  iii) R is a gene encoding the *Lactobacillus delbrueckii* subsp. *lactis* lac repressor protein that is SEQ ID NO: 2;
and wherein n denotes an integer $\geq 1$ and y denotes 0 or 1.

2. The DNA expression construct according to claim 1 wherein y is 1.

3. The DNA expression construct according to claim 1 wherein the reading frame of the gene coding for the lac repressor is reversed relative to the region p/o.

4. The DNA expression construct according to claim 1 wherein the gene coding for a polypeptide of interest is selected from the group consisting of genes encoding enzymes, and cell surface proteins.

5. The DNA expression construct according to claim 4 wherein the gene coding for the polypeptide of interest is selected from the group consisting of genes coding for dextransucrase, glycosyltransferase, phytase, transglutaminase, peptidase, phenylalanine ammonia lyase, protease, cell surface antigens, bacteriocins, hormones and insulin.

6. An isolated DNA sequence encoding the lac repressor protein of *Lactobacillus delbrueckii* subsp. *lactis* as identified by SEQ ID NO: 2.

7. A recombinant microorganism transformed with a DNA expression construct according to claim 1.

8. The recombinant microorganism according to claim 7 wherein the recombinant microorganism is a gram positive bacterium.

9. The recombinant microorganism according to claim 7 wherein the recombinant microorganism is lactic acid bacteria.

10. The recombinant microorganism according to claim 7 wherein the DNA sequence is incorporated into the microorganism's chromosome.

11. The recombinant microorganism according to claim 7 wherein the DNA sequence is transformed in a plasmid maintained extra-chromosomally.

12. The recombinant microorganism according to claim 7 wherein the DNA expression construct is a plasmid.

13. A method of producing a polypeptide comprising the steps of:

transforming a host cell with an isolated DNA expression construct comprising a DNA sequence represented by a general formula selected from the group consisting of:

$$p/o\text{-}(A)_n\text{-}R_y, \text{ and}$$

$$p/o\text{-}R_y\text{-}(A)_n$$

wherein
  i) p/o is a *Lactobacillus delbrueckii* subsp. *lactis* promoter that is SEQ ID NO: 9,
  ii) A is a heterologous gene encoding a polypeptide of interest; and
  iii) R is a gene encoding the *Lactobacillus delbrueckii* subsp. *lactis* lac repressor protein that is SEQ ID NO: 2,
and wherein n denotes an integer $\geq 1$ and y denotes 0 or 1; and
  culturing the host cell under conditions favorable to the expression of the polypeptide of interest wherein expression is performed in presence of lactose.

14. The method according to claim 13 wherein the DNA sequence is transformed in a plasmid maintained extra-chromosomally.

15. The method according to claim 13 wherein expression is performed in a gram positive microorganism in presence of lactose.

16. The method according to claim 13 wherein expression is performed in a lactic acid bacteria in presence of lactose.

17. A method for the production of food products comprising the steps of:

transforming a host cell with an isolated DNA expression construct comprising a DNA sequence represented by a general formula selected from the group consisting of:

p/o-(A)$_n$-R$_y$, and p/o-R$_y$-(A)$_n$ wherein
i) p/o is a *Lactobacillus delbrueckii* subsp. *lactis* promoter that is SEQ ID NO: 9,
ii) A is a heterogous gene encoding a polypeptide of interest; and
iii) R is a gene encoding the *Lactobacillus delbrueckii* subsp. *lactis* lac repressor protein that is SEQ ID NO: 2, and wherein n denotes an integer $\geq 1$ and y denotes 0 or 1; and using the host cell in the production of food products.

* * * * *

SEQUENCE LISTING

<160> NUMBER OF SEQ ID NOS: 33

<210> SEQ ID NO 1
<211> LENGTH: 1435
<212> TYPE: DNA
<213> ORGANISM: Lactobacillus delbrueckii

<400> SEQUENCE: 1

```
gaattttgtc tggatgctca ggaagcccgc cagctcaagc tggtgattca gccacttttt      60
actgaataat gctacaattg acttaacagc ataaaatttt agtaaaagcg agtgaagaag     120
atggcaacga tcagagaagt ggccaaggca gccggcgtgt cgccagcgac ggtttcccgg     180
gtcttgaact atgaccagac cctgtcggtc aatgaggcaa cgcggcagaa gatattcaaa     240
actgctgaag ccatgcacta ccataagagc cggaagacca gaaagagcaa gcaaaagcgc     300
ctggcgatct gcctgtggtg tgaccaagac caggagatca aggacctcta ttactattca     360
atcagaacca gcgcgcaagc agaggccaag aagcagggac ttgaaagcca ggtcatttat     420
ccggctgatc ctttgcccga tccagctgct ttaagcggga ttatcatgat tggctaccag     480
cagtattcgc cagaccgctt gaatgaagtc aaaaagtctg gcctgcccct ggtctttgtc     540
gatactgaca ccttaaaatt gggttactgc tcagttgtgg ctgactttgg ccaggccatg     600
caggaggcgc tagaggtctt ctgggggcag ggcagggagc ggatcgccct tttggatggt     660
gatttggaca gtaattttga taaaaacaac ttggtcgact tccgcttccg cgattataag     720
```

-continued

```
aagagcctcg cggcccgcgg ccagtacgac ccggacttag tctatgttgg aaacttcact    780
ccgcaatctg gctatgaagc cattaaagaa gctcttaagt ccggctcctt cccgaaagcc    840
ttgattgcgg ctaatgacgc catggctatt ggagcattga aggcctttaa agaagctgga    900
attaaagtcc cagaggacgt cagtctgatt tcttttaatg acacaacggc agcagaattt    960
gccaacccag ccttgactag cgtacatgta gagacccagc agatgggccg agccagcgtc   1020
aaggtcatga aagacctgct ggatgatgat gaagccggca cttacaaggt cactttccca   1080
acaaaactcg tttaccggga atcttgccca aaagcataag gcatagagc ataataacag    1140 caaagaaata gcttggagat tgattttctc caagctattt ttcgtatata ttatggctgc   1200
attctgttga tcattcttgg gaatgggaca gcttcacgaa cgtggtccag cttgcagatc   1260
caggcaatga cccgttcaaa gcccatcccg aagccggagt gcggcacgtg ccgtactttt   1320
ctcagggtcc caggtaccca ggagtagtcg tcccagggtt gaggcccgct tcttcgattt   1380
gcgccttcaa ggtgtcgtag tcagcttcac gttctgatcc gccatgattt cccgt         1435
```

<210> SEQ ID NO 2
<211> LENGTH: 332
<212> TYPE: PRT
<213> ORGANISM: Lactobacillus delbrueckii

<400> SEQUENCE: 2

```
Met Ala Thr Ile Arg Glu Val Ala Lys Ala Ala Gly Val Ser Pro Ala
1               5                   10                  15

Thr Val Ser Arg Val Leu Asn Tyr Asp Gln Thr Leu Ser Val Asn Glu
            20                  25                  30

Ala Thr Arg Gln Lys Ile Phe Lys Thr Ala Glu Ala Met His Tyr His
        35                  40                  45

Lys Ser Arg Lys Thr Arg Lys Ser Lys Gln Lys Arg Leu Ala Ile Cys
    50                  55                  60

Leu Trp Cys Asp Gln Asp Gln Glu Ile Lys Asp Leu Tyr Tyr Tyr Ser
65                  70                  75                  80

Ile Arg Thr Ser Ala Gln Ala Glu Ala Lys Lys Gln Gly Leu Glu Ser
                85                  90                  95

Gln Val Ile Tyr Pro Ala Asp Pro Leu Pro Asp Pro Ala Ala Leu Ser
            100                 105                 110

Gly Ile Ile Met Ile Gly Tyr Gln Gln Tyr Ser Pro Asp Arg Leu Asn
        115                 120                 125

Glu Val Lys Lys Ser Gly Leu Pro Leu Val Phe Val Asp Thr Asp Thr
    130                 135                 140

Leu Lys Leu Gly Tyr Cys Ser Val Val Ala Asp Phe Gly Gln Ala Met
145                 150                 155                 160

Gln Glu Ala Leu Glu Val Phe Trp Gly Gln Gly Arg Glu Arg Ile Ala
                165                 170                 175

Leu Leu Asp Gly Asp Leu Asp Ser Asn Phe Asp Lys Asn Asn Leu Val
            180                 185                 190

Asp Phe Arg Phe Arg Asp Tyr Lys Lys Ser Leu Ala Ala Arg Gly Gln
        195                 200                 205

Tyr Asp Pro Asp Leu Val Tyr Val Gly Asn Phe Thr Pro Gln Ser Gly
    210                 215                 220

Tyr Glu Ala Ile Lys Glu Ala Leu Lys Ser Gly Ser Phe Pro Lys Ala
225                 230                 235                 240

Leu Ile Ala Ala Asn Asp Ala Met Ala Ile Gly Ala Leu Lys Ala Phe
                245                 250                 255
```

-continued

Lys Glu Ala Gly Ile Lys Val Pro Glu Asp Val Ser Leu Ile Ser Phe
              260                 265                 270

Asn Asp Thr Thr Ala Ala Glu Phe Ala Asn Pro Ala Leu Thr Ser Val
        275                 280                 285

His Val Glu Thr Gln Gln Met Gly Arg Ala Ser Val Lys Val Met Lys
    290                 295                 300

Asp Leu Leu Asp Asp Glu Ala Gly Thr Tyr Lys Val Thr Phe Pro
305                 310                 315                 320

Thr Lys Leu Val Tyr Arg Glu Ser Cys Pro Lys Ala
                325                 330

<210> SEQ ID NO 3
<211> LENGTH: 6
<212> TYPE: DNA
<213> ORGANISM: Lactobacillus delbrueckii

<400> SEQUENCE: 3 tgttta                                                          6

<210> SEQ ID NO 4
<211> LENGTH: 7
<212> TYPE: DNA
<213> ORGANISM: Lactobacillus delbrueckii

<400> SEQUENCE: 4 gtaaaca                                                         7

<210> SEQ ID NO 5
<211> LENGTH: 7
<212> TYPE: DNA
<213> ORGANISM: Lactobacillus delbrueckii

<400> SEQUENCE: 5 gtaaacg                                                         7

<210> SEQ ID NO 6
<211> LENGTH: 17
<212> TYPE: DNA
<213> ORGANISM: Lactobacillus delbrueckii

<400> SEQUENCE: 6
cgcctggtga ttcagcc                                              17

<210> SEQ ID NO 7
<211> LENGTH: 20
<212> TYPE: DNA
<213> ORGANISM: Lactobacillus delbrueckii

<400> SEQUENCE: 7
agctttacgg ggaagtcggg                                           20

<210> SEQ ID NO 8
<211> LENGTH: 15
<212> TYPE: DNA
<213> ORGANISM: Lactobacillus delbrueckii

<400> SEQUENCE: 8
tgtaagcgta aacaa                                                15

<210> SEQ ID NO 9
<211> LENGTH: 98

```
<212> TYPE: DNA
<213> ORGANISM: Lactobacillus delbrueckii

<400> SEQUENCE: 9
tgtttactaa aaatattttg gtaaagcatc ttgatttgtt tagtaaacgg gtctatactg      60
taagcgtaaa caagttagaa cacctaaagg agaaaatc                             98

<210> SEQ ID NO 10
<211> LENGTH: 25
<212> TYPE: DNA
<213> ORGANISM: Lactobacillus delbrueckii

<400> SEQUENCE: 10
atattactgc agagtaaaag cgagt                                           25

<210> SEQ ID NO 11
<211> LENGTH: 25
<212> TYPE: DNA
<213> ORGANISM: Lactobacillus delbrueckii

<400> SEQUENCE: 11
ataaataagc ttacagaatg cagcc                                           25

<210> SEQ ID NO 12
<211> LENGTH: 27
<212> TYPE: DNA
<213> ORGANISM: Lactobacillus delbrueckii

<400> SEQUENCE: 12
atattagaat tcagtgactt aaactgg                                         27

<210> SEQ ID NO 13
<211> LENGTH: 27
<212> TYPE: DNA
<213> ORGANISM: Lactobacillus delbrueckii

<400> SEQUENCE: 13
atattagaat tcagtacttt gacaccg                                         27

<210> SEQ ID NO 14
<211> LENGTH: 27
<212> TYPE: DNA
<213> ORGANISM: Lactobacillus delbrueckii

<400> SEQUENCE: 14
atattagaat tcaagaggct atatcgc                                         27

<210> SEQ ID NO 15
<211> LENGTH: 18
<212> TYPE: DNA
<213> ORGANISM: Lactobacillus delbrueckii

<400> SEQUENCE: 15
ggttaatgcc gccaaagt                                                   18

<210> SEQ ID NO 16
<211> LENGTH: 25
<212> TYPE: DNA
<213> ORGANISM: Lactobacillus delbrueckii

<400> SEQUENCE: 16
ataaatctgc agtgggtatg gtggc                                           25
```

```
<210> SEQ ID NO 17
<211> LENGTH: 22
<212> TYPE: DNA
<213> ORGANISM: Lactobacillus delbrueckii

<400> SEQUENCE: 17
gatcgttgcc acattcacca cc                                              22

<210> SEQ ID NO 18
<211> LENGTH: 21
<212> TYPE: DNA
<213> ORGANISM: Lactobacillus delbrueckii

<400> SEQUENCE: 18
ggtgaatgtg gcaacgatca g                                               21

<210> SEQ ID NO 19
<211> LENGTH: 25
<212> TYPE: DNA
<213> ORGANISM: Lactobacillus delbrueckii

<400> SEQUENCE: 19
atattactgc agacagaatg cagcc                                           25

<210> SEQ ID NO 20
<211> LENGTH: 25
<212> TYPE: DNA
<213> ORGANISM: Lactobacillus delbrueckii

<400> SEQUENCE: 20
ataaatctcg agtggtgatt cagcc                                           25

<210> SEQ ID NO 21
<211> LENGTH: 25
<212> TYPE: DNA
<213> ORGANISM: Lactobacillus delbrueckii

<400> SEQUENCE: 21
atattactcg agacagaatg cagcc                                           25

<210> SEQ ID NO 22
<211> LENGTH: 28
<212> TYPE: DNA
<213> ORGANISM: Lactobacillus delbrueckii

<400> SEQUENCE: 22
tgtttactaa aaatatttg gtaaagca                                         28

<210> SEQ ID NO 23
<211> LENGTH: 28
<212> TYPE: DNA
<213> ORGANISM: Lactobacillus delbrueckii

<400> SEQUENCE: 23
tgtttactaa aagtatttg gtaaaaca                                         28

<210> SEQ ID NO 24
<211> LENGTH: 28
<212> TYPE: DNA
<213> ORGANISM: Lactobacillus delbrueckii

<400> SEQUENCE: 24
tggcgactaa aagtatttg gtaaaaca                                         28
```

<210> SEQ ID NO 25
<211> LENGTH: 28
<212> TYPE: DNA
<213> ORGANISM: Lactobacillus delbrueckii

<400> SEQUENCE: 25
aaattactaa aaatatttta gtaaaaca                                28

<210> SEQ ID NO 26
<211> LENGTH: 29
<212> TYPE: DNA
<213> ORGANISM: Lactobacillus delbrueckii

<400> SEQUENCE: 26
tcttgatttg tttagtaaac gggtctata                               29

<210> SEQ ID NO 27
<211> LENGTH: 29
<212> TYPE: DNA
<213> ORGANISM: Lactobacillus delbrueckii

<400> SEQUENCE: 27
tcttgatttg tttagtaaac aagtctata                               29

<210> SEQ ID NO 28
<211> LENGTH: 29
<212> TYPE: DNA
<213> ORGANISM: Lactobacillus delbrueckii

<400> SEQUENCE: 28
tcttgatttg tttagtaaac aagtctata                               29

<210> SEQ ID NO 29
<211> LENGTH: 29
<212> TYPE: DNA
<213> ORGANISM: Lactobacillus delbrueckii

<400> SEQUENCE: 29
tcttggttta tttagtaaac aagtctata                               29

<210> SEQ ID NO 30
<211> LENGTH: 107
<212> TYPE: DNA
<213> ORGANISM: Lactobacillus delbrueckii

<400> SEQUENCE: 30
tttttgttta ctaaaaatat tttggtaaag catcttgatt tgtttagtaa acgggtctat    60
actgtaagcg taaacaagtt agaacaccta aaggagaaaa tcatgaa               107

<210> SEQ ID NO 31
<211> LENGTH: 107
<212> TYPE: DNA
<213> ORGANISM: Lactobacillus delbrueckii

<400> SEQUENCE: 31
aaaaacaaat gatttttata aaaccatttc gtagaactaa acaaatcatt tgcccagata    60
tgacattcgc atttgttcaa tcttgtggat ttcctctttt agtactt                107

<210> SEQ ID NO 32
<211> LENGTH: 106
<212> TYPE: DNA

-continued

```
<213> ORGANISM: Lactobacillus delbrueckii

<400> SEQUENCE: 32
tttaaattac taaaaatatt ttagtaaaac atcttggttt atttagtaaa caagtctata      60
ctgtaattat aaacaagtta acacacctaa aggagaattt catgaa                   106

<210> SEQ ID NO 33
<211> LENGTH: 106
<212> TYPE: DNA
<213> ORGANISM: Lactobacillus delbrueckii

<400> SEQUENCE: 33
aaatttaatg atttttataa aatcatttg tagaaccaaa taaatcattt gttcagatat      60
gacattaata tttgttcaat tgtgtggatt tcctcttaaa gtactt                   106
```